United States Patent [19]
Rassman

[11] Patent Number: 5,817,120
[45] Date of Patent: Oct. 6, 1998

[54] HAIR IMPLANTING INSTRUMENT

[76] Inventor: William R. Rassman, c/o New Hair Institute, 9911 W. Pico Blvd., Suite 301, Los Angeles, Calif. 90035

[21] Appl. No.: 798,042

[22] Filed: Feb. 10, 1997

[51] Int. Cl.⁶ .................................................. A61B 17/34
[52] U.S. Cl. ........................................... 606/187; 606/185
[58] Field of Search ............................... 606/1, 167, 185, 606/187

[56] References Cited

U.S. PATENT DOCUMENTS

| | | |
|---|---|---|
| 3,945,117 | 3/1976 | Beaver . |
| 4,004,592 | 1/1977 | Yamada . |
| 4,126,124 | 11/1978 | Miller . |
| 4,451,254 | 5/1984 | Dinius et al. ............................ 604/62 |
| 5,417,683 | 5/1995 | Shiao ........................................ 606/1 |
| 5,439,475 | 8/1995 | Bennett ................................. 606/187 |
| 5,562,613 | 10/1996 | Kaldany ................................. 604/57 |
| 5,584,841 | 12/1996 | Rassman ............................... 604/132 |
| 5,584,851 | 12/1996 | Banuchi ................................ 606/187 |

FOREIGN PATENT DOCUMENTS

| | | |
|---|---|---|
| 733330 | 5/1966 | Canada . |
| 9212105 | 10/1992 | France . |
| 9405884 | 5/1994 | France . |
| 9509824 | 4/1995 | France . |
| 2231806 | 9/1984 | Germany . |
| 94/07433 | 4/1994 | WIPO . |

OTHER PUBLICATIONS

New Hair Newsletter, vol. 1, No. 3, New Hair Institute, Fall/Winter 1995.

Robert M. Bernstein, "Hair Restoration: Answered Questions.", Reprint from Dermatologic Surgery, vol. 22, 1996, pp. 97–98.

O'Tar T. Norwood, "Gearing Up for Two Thousand Grafts Per Session and Dense Packing", Hair Transplant Forum International, vol. 4, No. 4, Jul.–Aug. 1994.

William R. Rassman, "The Minigraft Revolution: Can We Keep Up Ethically?", Reprint from The American Journal of Cosmetic Surgery, vol. 11, No. 2, 1994, pp. 103–104.

New Hair Institute Update, except from Spring 1995 Newsletter, New Hair Institute.

(List continued on next page.)

*Primary Examiner*—Glenn K. Dawson
*Attorney, Agent, or Firm*—Fitzpatrick, Cella, Harper & Scinto

[57] ABSTRACT

An instrument for implanting hair grafts into a patient's scalp includes an elongate housing adapted to be manipulated by a surgeon during implanting of the hair grafts. The elongate housing has a throughbore extending at least partway therealong from a first end thereof, and has a loading position adjacent to the throughbore for loading hair grafts into the instrument. A cutting device is affixed to the first end of the elongate housing by which the surgeon may make an incision in the patient's scalp, into which a hair graft is to be implanted. In the instrument, an implanting member is disposed axially movably within the throughbore of the elongate housing, and includes a forwardly projecting finger. The implanting member is movable from a first position in which the finger is positioned adjacent to the loading position so as to be able to load a hair graft, to a second position in which a loaded hair graft is bounded between the finger and the cutting device, and to a third position in which the finger extends beyond the cutting device.

65 Claims, 22 Drawing Sheets

OTHER PUBLICATIONS

The Fast Track Option: A Common Sense Approach To Hair Transplantation, William R. Rassman, New Hair Institute, ©1994, 1995.

Hair Today And Tomorrow: An Overview of Old Wives Tales, Wigs, Lotions, Potions, Fact, Fiction and Medical Hair Restoration Options, Mar A. Pomerantz, et al., ©Aug., 1993.

Dominic A. Brandy, et al., "Utilization of No–Kor Needles for Slit–Micrografting", J. Dermatol. Surg. Oncol., No. 20, 1995, pp. 336–339.

James Arnold, "Pursuing the Perfect Strip: Harvesting Donor Strips with Minimal Hair Transection", International Journal of Aesthetic and Restorative Surgery, vol. 3, No. 2, 1995, pp. 148–153.

Robert M. Bernstein, et al., "Follicular Transplantation", International Journal of Aesthetic and Restorative Surgery, vol. 3, No. 2, 1995, pp. 119–132.

William R. Rassman, et al., "The Art and Science of Minigrafting", Reprint from International Journal of Aesthetic and Restorative Surgery, vol. 1, No. 1, 1993, pp. 27–36.

William R. Rassman, et al., "Micrografting in Extensive Quantities", Reprint from Dermatolgic Surgery, vol. 21, No. 4, Apr. 19, 1995, pp. 306–311.

William R. Rassman, "Megasessions: Dense Packing", Hair Transplant Forum International, vol. 4, No. 3, May–Jun. 1994.

Richard C. Shiell, "An Australian View of the Las Vegas Meeting", Hair Transplant Forum International, vol. 5, No. 5, Sep.–Oct. 1995.

Michael Beehner, "1995 Las Vegas ISHRS Meeting", Hair Transplant Forum International, vol. 5, No. 5, Sep.–Oct. 1995.

William R. Rassman, "One of our greatest problems . . . Lowballing!", Hair Transplant Forum International, vol. 2, No. 6, Jul.–Aug. 1992.

William R. Rassman, "Concern About Quality", Hair Transplant Forum International, vol. 4, No. 4, Jul.–Aug. 1994.

Michael D. Sparkuhl, "Hair Transplant Surgery: The Next Generation", Hair Transplant Forum International, vol. 4, No. 4, Jul.–Aug. 1994.

William R. Rassman, "Trouble With Megasessions and Dense Packing", Hair Transplant Forum, vol. 5, No. 6, Nov.–Dec. 1995.

Robert M. Bernstein, et al., "Laser Hair Transplantation: Is it really State–of–the–Art?", Laser in Surgery and Medicine, vol. 19, No. 2 1996.

Richard C. Shiell, "Megasessions: The Dense Packing Of Micrografts Proves A Most Effective Technique", Hair Transplant Forum International, vol. 6, No. 5, Sep.–Oct. 1995.

Robert M. Bernstein, "Are Scalp Reductions Still Indicated?", Hair Transplant Forum International, vol. 6, 1996.

A Buyer's Guide To Hair Transplantation: The Answers Are In The Details, William R. Rassman, New Hair Institute, ©1993.

Videotape entitled "New Hair: The Trauth About Transplants", New Hair Institute, © 1993.

New Hair Institute News, vol. 2, No. 1, New Hair Institute, Spring/Summer 1996.

Everything You Ever Wanted To Know About Hair Transplantation But Were Afraid To Ask, William R. Rassman, New Hair Institute, ©1993.

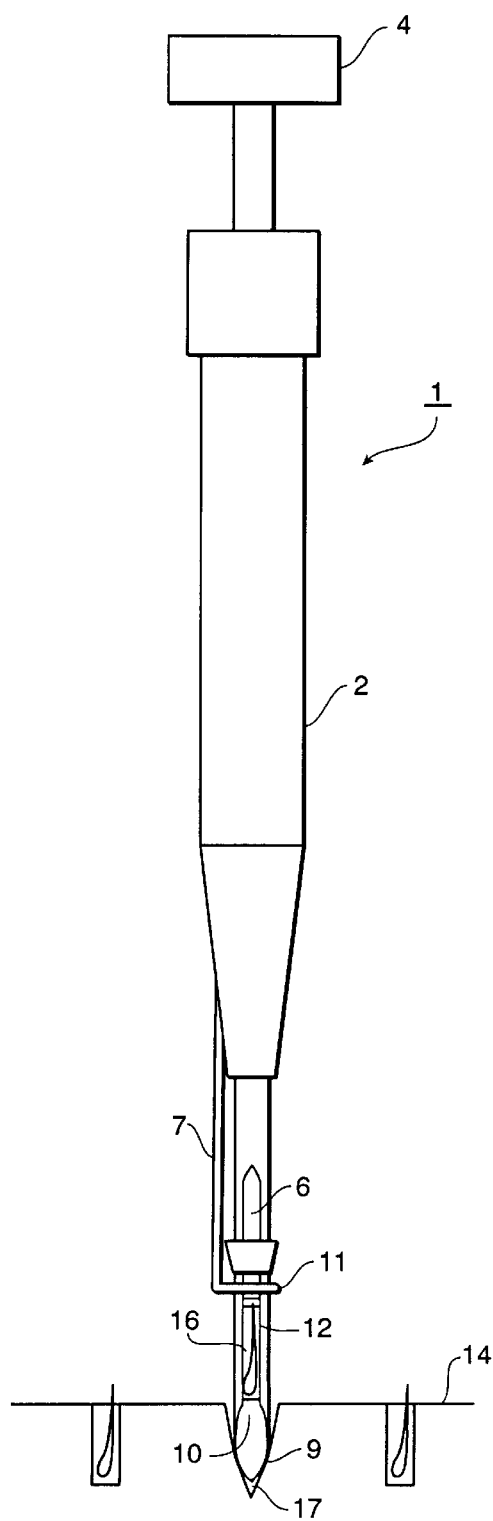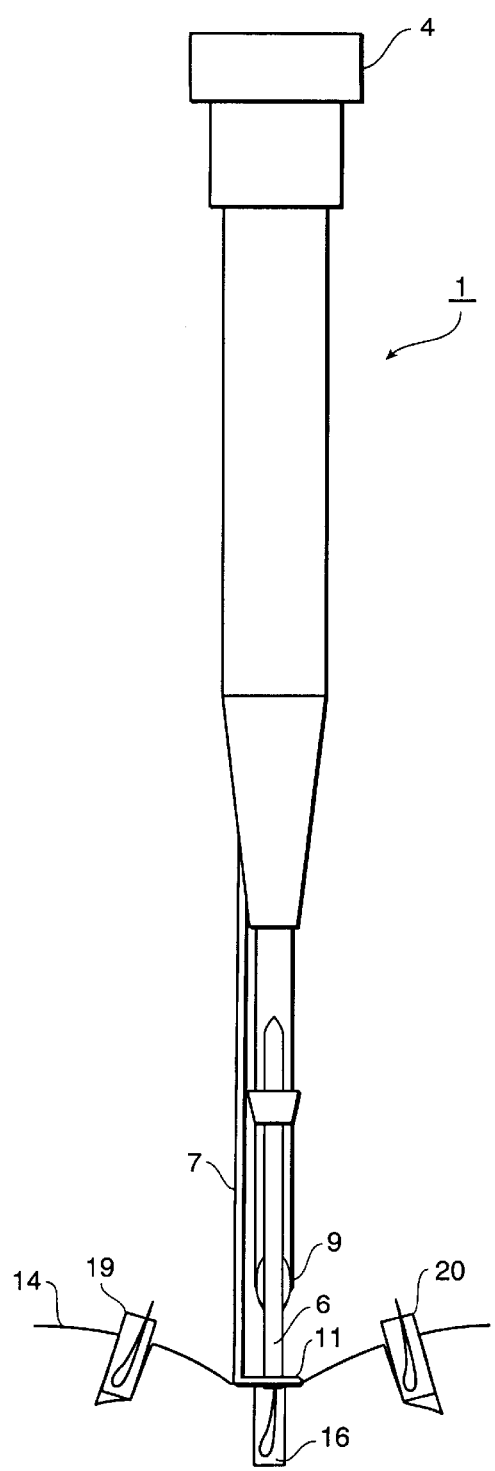
FIG. 1A
(Prior Art)
FIG. 1B
(Prior Art)

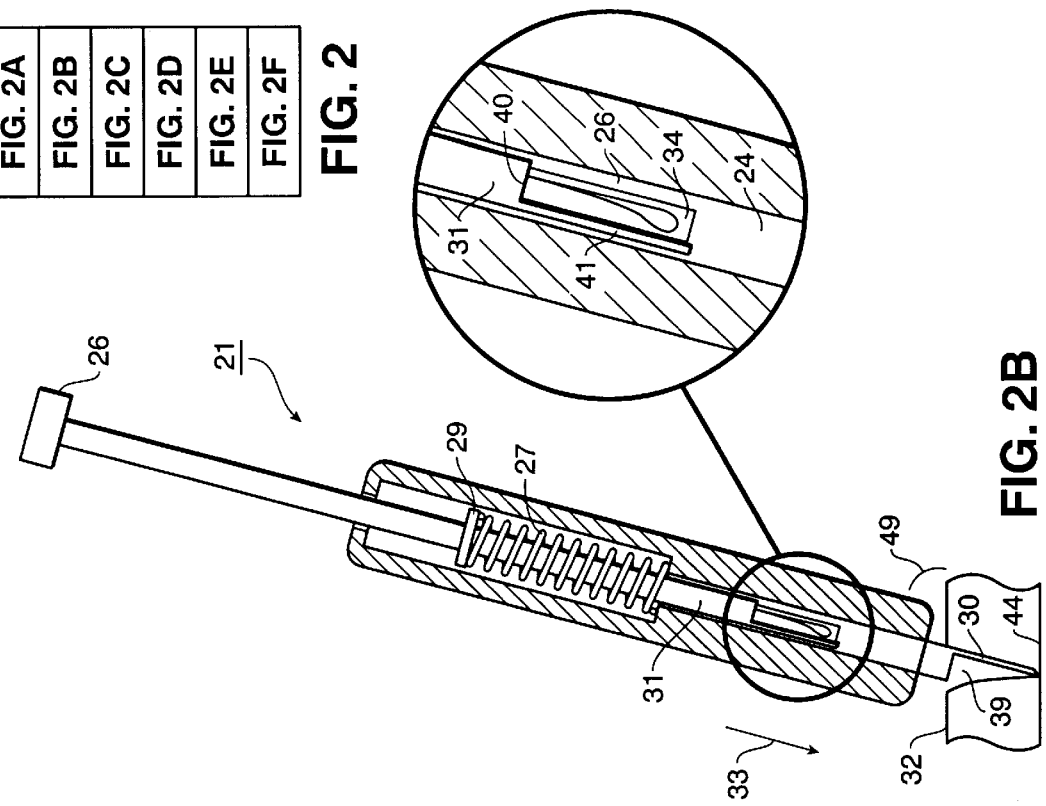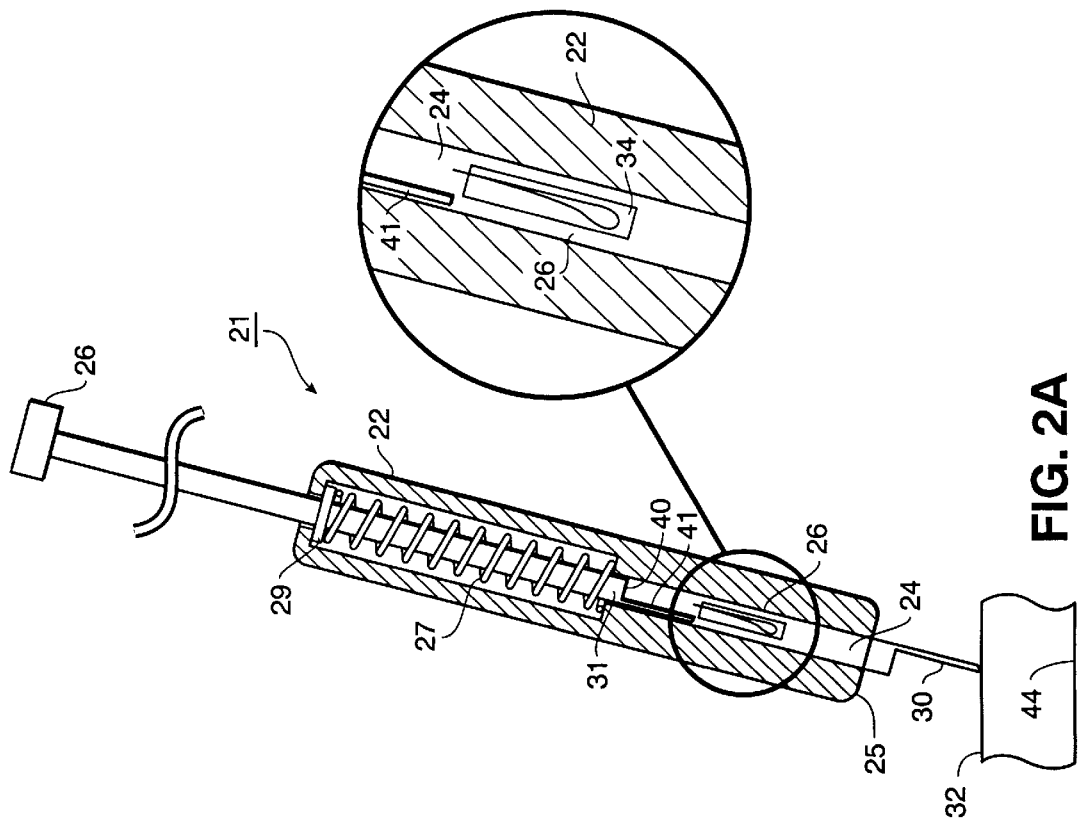

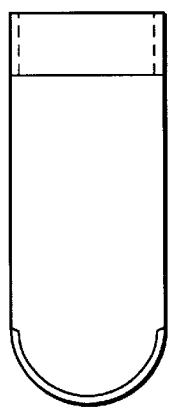 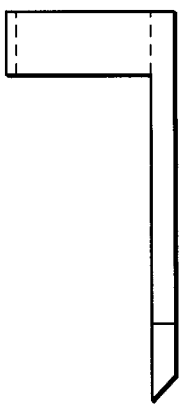 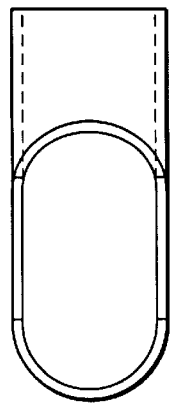 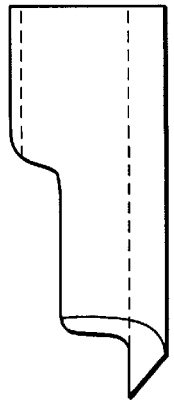
FIG. 5A  FIG. 5B    FIG. 6A  FIG. 6B
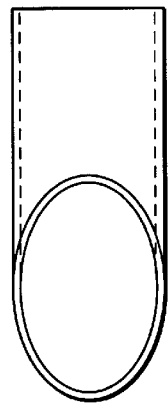 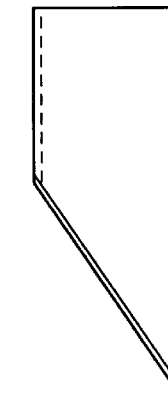 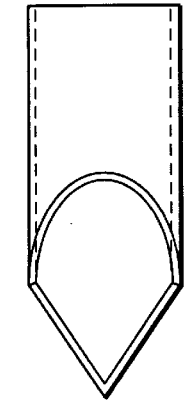 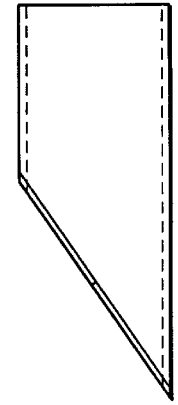
FIG. 7A  FIG. 7B    FIG. 8A  FIG. 8B
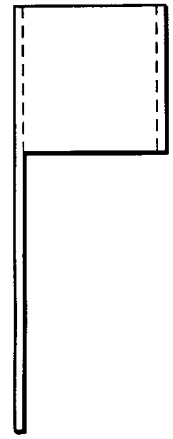 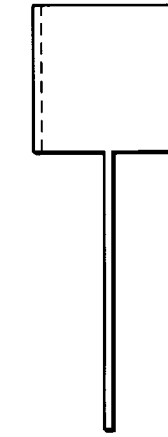 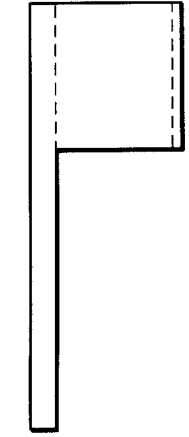 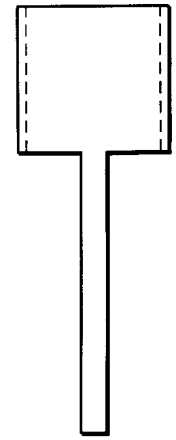
FIG. 9A  FIG. 9B    FIG. 10A  FIG. 10B

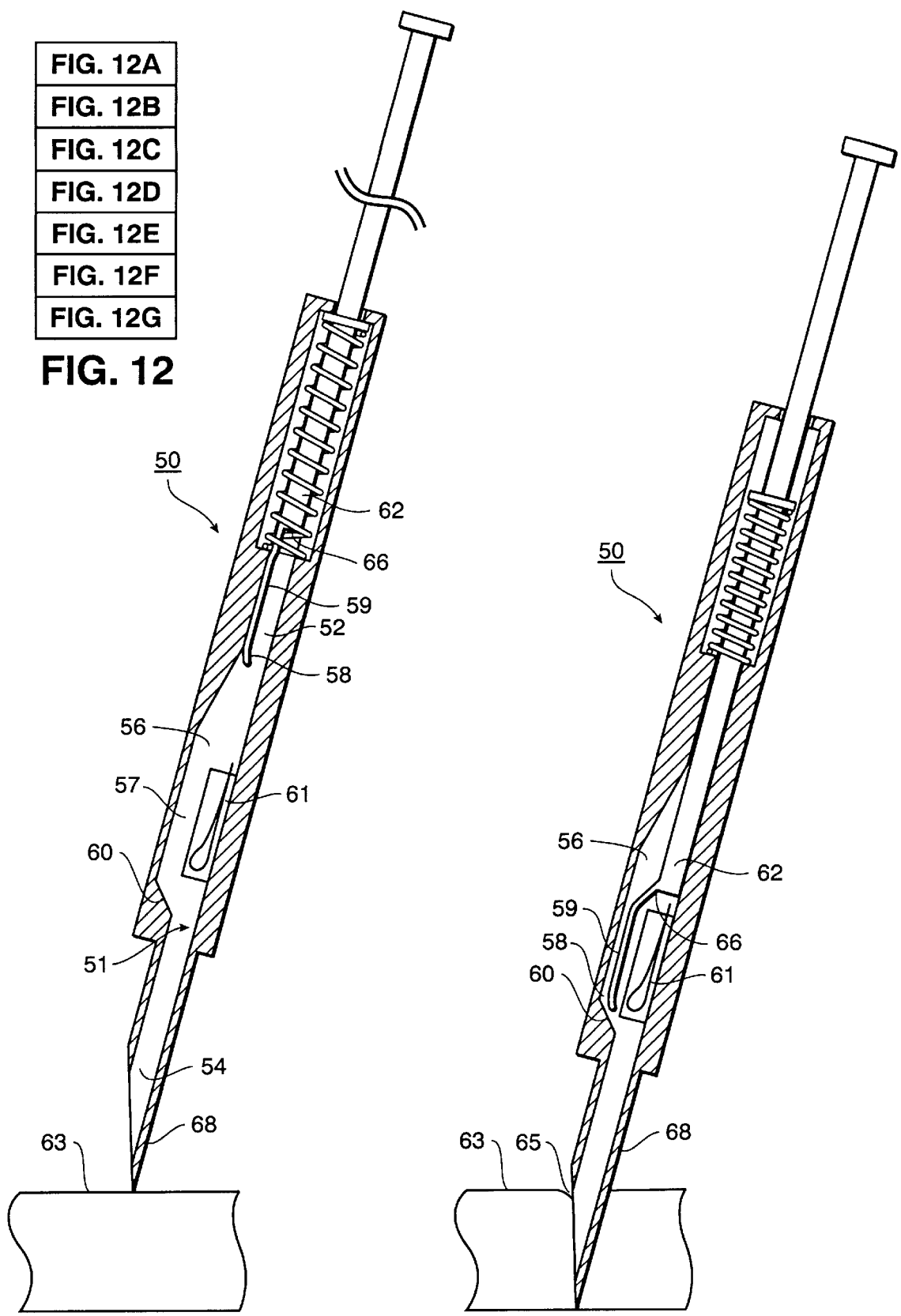

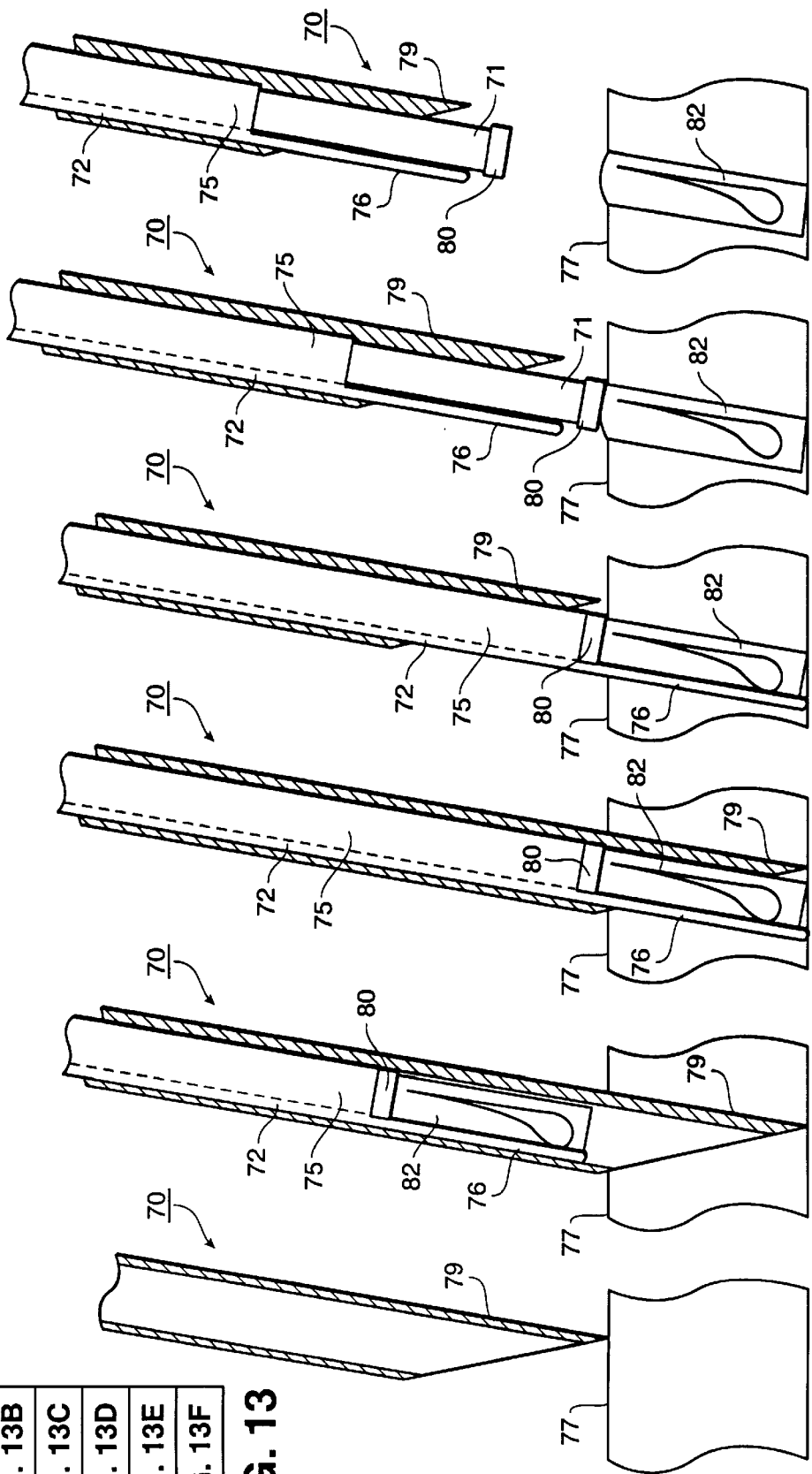

HAIR IMPLANTING INSTRUMENT

BACKGROUND OF THE INVENTION

1. Field of the Invention

The present invention relates to an instrument for implanting hair grafts, and a method for use therewith, which includes a cutting device for making an incision in a patient's scalp, and an implanting member. The implanting member picks up a hair graft from a load position, and moves the hair graft into the incision such that the hair graft is bounded between a finger projecting from the implanting member and the cutting device. The cutting device then withdraws, followed by the finger, leaving the hair graft in the incision.

2. Description of the Related Art

As described in Applicant's co-pending U.S. patent application Ser. No. 08/630,244, entitled "Hair Transplantation System", hair transplantation procedures involve removing hair grafts from a donor region of a patient's scalp which contains permanently-growing hair, and implanting those hair grafts into a balding region of the patient's scalp.

In contrast to traditional procedures which transplanted large grafts containing up to 25 hair follicles per graft, modern hair transplantation procedures, such as follicular transplantation, transplant "follicular" grafts, which contain 1 to 4 hair follicles per graft. These smaller grafts are more fragile and, consequently, more difficult to handle than the larger grafts used in traditional procedures. As a result, modern hair transplantation procedures face new problems not addressed in traditional procedures.

For example, one problem faced by modern transplantation procedures has to do with maintaining the integrity of a hair graft during actual implantation into the scalp. More specifically, conventional hair transplantation procedures typically use an instrument which pushes a hair graft into an incision, such as the "Choi" instrument shown in FIGS. 1A and 1B. Due to their small size, however, follicular grafts are often compressed during the pushing action. This compression can cause the graft to be deformed and/or damaged during implantation.

One solution to the foregoing problem is provided in Applicant's U.S. Pat. No. 5,584,841, entitled "Instrument For Implanting Hair Grafts", which issued on Dec. 17, 1996. In that patent, Applicant describes an instrument for dragging hair grafts into an incision created in a patient's scalp. While the instrument described in that patent has its advantages, it does not provide a means for maintaining the integrity of hair grafts during and after implantation, as does the present invention described below Another problem faced in modern hair transplantation procedures is illustrated with respect to the conventional hair implanting instrument shown in FIGS. 1A and 1B. As shown in FIG. 1A, instrument 1 includes housing 2, plunger 4, implanting rod 6, extracting member 7, and cutting device 9. Cutting device 9 includes bore 10, into which hair grafts are loaded, and extracting member 7 includes foot 11, used to extract cutting device 9 from an incision. Implanting rod 6 is physically joined to extracting member 7 via channel 12, such that the two move in synchronism.

FIGS. 1A and 1B show operation of instrument 1 during a conventional hair transplantation procedure. As shown in the figures, cutting device 9 makes an incision into patient's scalp 14. Plunger 4 is then actuated, thereby causing implanting rod 6 to force hair graft 16 out of bore 10 and into incision 17. This pushing action can compress the hair graft in the incision, particularly if the incision is not sufficiently deep, thereby resulting in deformation and/or damage to the hair graft.

At the same time that implanting rod 6 pushes the hair graft into incision 17, extracting member 7 moves downwardly, putting pressure on patient's scalp 14 via foot 11. This, in turn, causes cutting device 9 to withdraw from incision 17, as shown in FIG. 1B. However, as also shown in FIG. 1B, the pressure put on patient's scalp 14 by foot 11 can adversely affect nearby hair grafts. That is, the downward pressure on patient's scalp 14 applied by foot 11 forces nearby areas of the scalp upward, thereby forcing hair grafts, such as grafts 19 and 20, in those nearby areas to extrude from their incisions. This problem is particularly acute in areas of the scalp in which hair grafts have been implanted closely together.

Thus, as demonstrated by the foregoing example, there exists a need for a hair implanting instrument that can implant a hair graft into an incision without significantly deforming or damaging the hair graft, and that can withdraw from the incision without significantly adversely affecting the implanted hair graft or those around it.

SUMMARY OF THE INVENTION

The present invention addresses the foregoing need by providing an instrument for implanting hair grafts which includes a cutting device and an implanting member having a blunt end and a finger extending forwardly beyond the blunt end. The implanting member is movable from a first position, in which the hair graft is loaded, to a second position, in which the hair graft is bounded between the finger and the cutting device, and to a third position, in which the finger extends beyond the cutting device.

During a hair transplantation procedure using the invention, a hair graft is moved by the implanting member from the first position into an incision in a patient's scalp. As the finger moves into the incision, the finger opens the incision to allow the finger and the hair graft to advance forward with little resistance. In the incision, the implanting member is in the second position, such that the hair graft is bounded by the finger and the cutting device. Thereafter, the implanting member is moved to the third position, in which the cutting device has been withdrawn from the incision, leaving the finger and the hair graft in the incision. Finally, the finger is withdrawn from the incision, leaving only the hair graft. Preferably, the finger is relatively narrow, so as to reduce the chances that the hair graft will extrude from the incision during withdrawal of the finger.

By bounding the hair graft in the incision between the finger and the cutting device, the invention provides a protective sheath at least part way around the hair graft, thereby lessening the chances that the hair graft will be deformed and/or damaged, even during pushing into the incision. Moreover, by providing a finger which extends beyond the cutting device and which remains in the incision following withdrawal of the cutting device, the invention provides means for retaining the hair graft in the incision during withdrawal of the cutting device. Thus, the invention reduces the chances that the hair graft will be withdrawn from the incision during withdrawal of the cutting device.

Moreover, during withdrawal of the cutting device, the finger transfers forces applied to the instrument to the patient's skull. As a result, pressure is not applied to the patient's scalp during withdrawal of the cutting device. Thus, the invention also reduces extrusion of surrounding hair grafts during withdrawal of the cutting device from the incision.

According to one aspect, the present invention is an instrument for implanting hair grafts into a patient's scalp, which includes an elongate housing adapted to be manipulated by a surgeon during implanting of the hair grafts. The elongate housing has a throughbore extending at least partway therealong from a first end thereof, and has a loading position adjacent to the throughbore for loading hair grafts into the instrument. A cutting device is affixed to the first end of the elongate housing by which the surgeon may make an incision in the patient's scalp, into which a hair graft is to be implanted. In the instrument, an implanting member is disposed axially movably within the throughbore of the elongate housing, and includes a forwardly projecting finger. The implanting member is movable from a first position in which the finger is positioned adjacent to the loading position so as to be able to load a hair graft, to a second position in which a loaded hair graft is bounded between the finger and the cutting device, and to a third position in which the finger extends beyond the cutting device.

In particularly preferred embodiments of the invention, the implanting member includes a blunt end which the finger projects beyond. In such embodiments, the blunt end has a cross-sectional area which is greater than a cross-sectional area of the finger. By including a blunt end which has a relatively large cross-sectional area, the invention facilitates implanting of grafts into the incision, e.g., through pushing via the blunt end. In addition, by providing a finger which has a relatively small cross-sectional area, e.g., which is relatively narrow, the invention reduces the amount of frictional drag which may occur during withdrawal of the finger from the incision, thereby reducing the chances that a hair graft implanted in the incision will be pulled out during withdrawal.

In other particularly preferred embodiments of the invention, the throughbore includes at least one narrow segment and a wide segment which is adjacent to the loading position. In these embodiments, the finger is fabricated from a springy material and is spring-loaded in the throughbore. Thus, in the wide segment, the finger is freed to expand.

By virtue of the foregoing features, the invention facilitates loading of the hair graft into the incision. That is, because the finger can expand in the wide segment of the throughbore, the finger can more easily slide adjacent to a hair graft in the loading position. As a result, damage to hair grafts during loading is reduced.

In embodiments of the invention in which the throughbore has both narrow and wide segments, the invention preferably includes a camber which has an inclined surface, positioned at an end of the loading position, which is capable of guiding the finger from the wide segment of the throughbore into a narrow segment of the throughbore. Preferably, the camber is gradually sloped downwardly from the wide segment to the narrow segment. In this manner, the camber facilitates movement of the finger into the narrow segment, as well as reduces the chances that the hair graft will be damaged during such action.

In embodiments of the foregoing type, the finger preferably has a tip which is curved relative to an axis of the throughbore. If the finger is shorter than the hair graft, then when it is spring-loaded inside the narrow segment of the throughbore, the tip can pinch the hair graft against an inner wall of the throughbore. This pinching action can assist in moving the hair graft into the incision. That is, in such a case, the finger assists in moving the hair graft by dragging the hair graft within the throughbore. As a result, the amount of pushing required to implant the hair graft and, consequently, the risk of damage resulting from such pushing, are reduced.

In addition, by pinching the hair graft with the finger in the manner described above, it is possible to fit the hair graft into relatively small incisions. This allows for placement of relatively small hair grafts, such as follicular grafts, much more efficiently than conventional instruments which do not pinch the hair graft.

Moreover, since the hair graft is made primarily of skin and fat, it is stretchable. Thus, when the hair graft is dragged into the incision, it is elongated. As a result, the width of the hair graft is reduced, making it easier to fit the hair graft into a smaller incision than if it were not stretched.

Alternatively, if the finger is longer than the hair graft, the tip of the finger inside the narrow segment shields the follicle-end of the hair graft. As a result, the chances of damage to the hair graft during loading are even further reduced.

While the finger may be made of a variety of materials, the finger is preferably made of a strong, flexible material, such as polycarbonate steel, which guards against breaking or shearing inside the incision. Preferably, the finger is fabricated such that the finger can transfer a predetermined amount of force to the patient's skull without breaking.

In still other particularly preferred embodiments of the invention, the implanting member includes a throughbore at least partway therethrough, and a holding member disposed within the throughbore, which is movable relative to the finger. In these embodiments, the holding member is movable from an unextended position, in which the holding member extends to less than a length of the finger, to an extended position, in which the holding member extends to greater than a length of the finger. By employing a holding member which is operable in such a manner, the invention provides a means for holding the hair graft in the incision during withdrawal of the finger. Thus, the invention reduces the chances of withdrawal of an implanted hair graft during withdrawal of the finger from the incision.

In a preferred embodiment of the invention, the elongate housing includes an upper portion, which houses a plunger used to control movement of the implanting member, and a lower portion, which includes the throughbore and the implanting member. In these embodiments, the upper portion includes a grabber which holds onto an end of the implanting member, and the implanting member comprises an elbow which extends therefrom. To hold onto the elbow, the grabber includes at least two jaws and a mouth, the two jaws being expandable to allow access by the elbow to the mouth.

The foregoing configuration is particularly advantageous in cases where the upper portion and the lower portion of the elongate housing are detachable from each other. That is, in such cases, one portion, preferably but not necessarily the lower portion, can be made disposable without requiring that the whole instrument be disposable. As a result, production costs and thus per unit costs can be decreased.

In particularly preferred embodiments of the foregoing invention, the lower portion includes a circular magazine adapted to receive a circular cartridge which holds hair grafts to be implanted, and the implanting member includes a blunt end which is separated from the finger by a slit therebetween.

In the above embodiments, preferably, at least a portion of the finger is curved relative to an axis of the throughbore, and the throughbore includes a wide segment adjacent to the loading position and a narrow segment which extends at least part way up from the cutting device. The finger is preferably fabricated from a springy material, and the instrument includes a camber at an end of the loading position to guide the finger from the wide segment to the narrow segment such that the finger is spring-loaded at least within the narrow segment.

By virtue of the foregoing configuration, it is possible to reduce the damage, described above, to hair grafts during implantation.

According to another aspect, the present invention is a method of implanting a hair graft from a hair implanting instrument into a patient's scalp. The method includes the steps of making an incision in the patient's scalp using a cutting device, into which a hair graft is to be implanted, and loading a hair graft into an implanting member in the hair implanting instrument, which is movable relative to the cutting device. The hair graft and a finger projecting from the implanting member are then moved into the incision such that the hair graft in the incision is bounded by the cutting device and the finger. A first withdrawing step withdraws the cutting device from the incision, and a second withdrawing step withdraws the finger from the incision.

By bounding the hair graft between the finger and the cutting device, it is possible to reduce damage and/or deformation to the hair graft during implantation. In addition, by maintaining the finger in the incision while the cutting device is withdrawn, the invention reduces that chances that an implanted hair graft will be inadvertently withdrawn from the incision during withdrawal of the cutting device.

In particularly preferred embodiments of the invention, the hair graft, which is wet with saline and plasma, "bonds" to the finger via surface tension. This bonding secures the hair graft to the finger, thus facilitating movement of the hair graft into the incision. More specifically, because the hair graft is "bonded" to the finger, a dragging force is created between the hair graft and the finger. This dragging force aids in the movement of the hair graft into the incision and, consequently, reduces the amount of pushing required for such movement.

In other particularly preferred embodiments of the invention, the step of moving the hair graft into the incision includes pinching the hair graft between a curved tip of the finger and an inner wall of a throughbore in which the implanting member moves, and dragging the hair graft into the incision using the finger while at the same time pushing the hair graft into the incision using a blunt end of the implanting member. By applying both pushing and dragging forces to move the hair graft into the incision, the invention reduces overall damage which may be done to the hair graft during the implantation process.

In other particularly preferred embodiments of the invention, the moving step moves the finger into the incision so that the finger contacts the patient's skull. In these embodiments, the step of withdrawing the cutting device from the incision includes applying downward force to the finger against the patient's skull, and lifting the cutting device out of the incision in response to the downward force applied to the finger, leaving the hair graft and the finger in the incision. In these embodiments, the downward force used to lift the cutting device is transmitted to the patient's skull rather than to skin on the scalp, unlike in the conventional instrument shown in FIGS. 1A and 1B. Accordingly, the invention reduces the chances that the implanted hair graft will be withdrawn from the patient's scalp during withdrawal of the cutting device, without causing significant extrusion of neighboring implanted hair grafts.

Thus, as described above, as the finger makes contact with the patient's skull, withdrawal of the cutting device results as continued pressure is applied to the finger and thus to the skull via the finger. As noted, this forces the cutting device from the incision, leaving the hair graft in the incision along with the finger such that the hair graft is left in the incision at a fixed position relative to the patient's skull.

This brief summary has been provided so that the nature of the invention may be understood quickly. A more complete understanding of the invention can be obtained by reference to the following detailed description of the preferred embodiments thereof in connection with the attached drawings.

BRIEF DESCRIPTION OF THE DRAWINGS

FIGS. 1A and 1B show front views of operation of a prior art hair implanting instrument during a conventional hair transplantation procedure.

FIGS. 5A and 5B show front and side views, respectively, of a flat blade cutting device which can be used in the hair implanting instrument of the present invention.

FIGS. 6A and 6B show front and side views, respectively, of a half-round needle cutting device which can be used in the hair implanting instrument of the present invention.

FIGS. 7A and 7B show front and side views, respectively, of a round needle cutting device which can be used in the hair implanting instrument of the present invention.

FIGS. 8A and 8B show front and side views, respectively, of a pointed (Nokor) needle cutting device which can be used in the hair implanting instrument of the present invention.

FIGS. 9A and 9B show side and front views, respectively, of a preferred embodiment of an implanting member having a finger projecting forwardly therefrom, which can be used in the hair implanting instrument of the present invention.

FIGS. 10A and 10B show side and front views, respectively, of a less narrow, less preferred embodiment of an implanting member having a finger projecting forwardly therefrom, which can be used in the hair implanting instrument of the present invention.

FIG. 13, comprised of FIGS. 13A, 13B, 13C, 13D, 13E and 13F, shows side views of a third embodiment of the hair implanting instrument of the present invention during various stages of a hair transplantation procedure.

DETAILED DESCRIPTION OF THE PREFERRED EMBODIMENTS

Figure 2D:
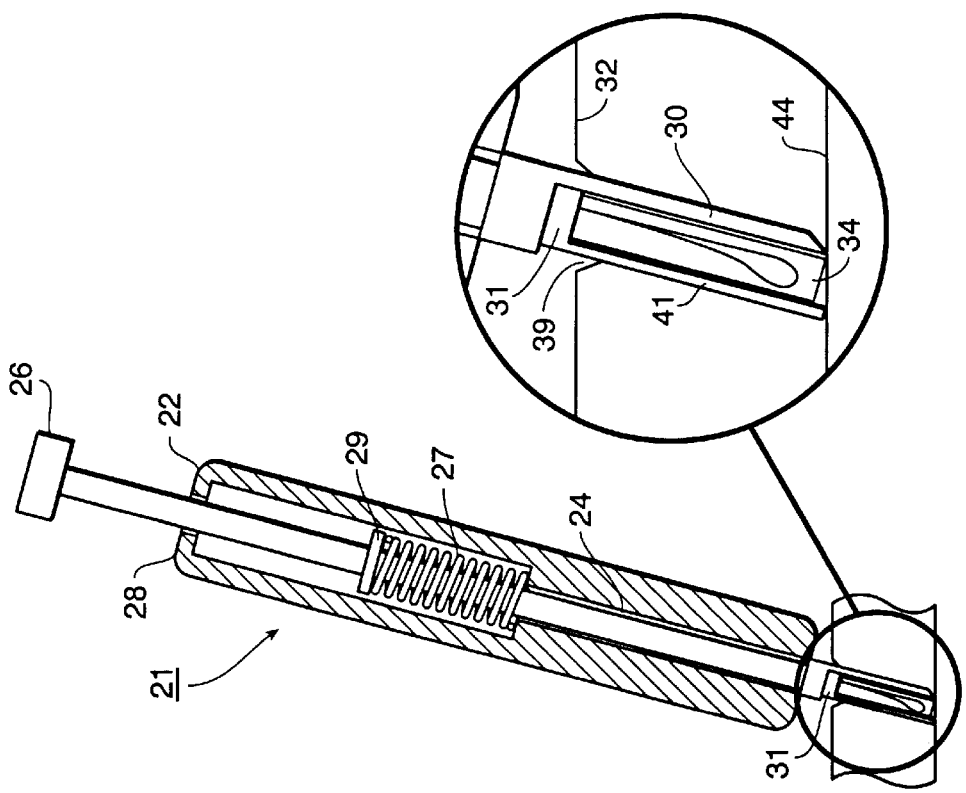
FIG. 2, comprised of FIGS. 2A, 2B, 2C, 2D, 2E and 2F, shows side views of a first embodiment of the hair implanting instrument of the present invention during various stages of a hair transplantation procedure.

In brief, the present invention is an instrument for implanting hair grafts into a patient's scalp, which includes an elongate housing adapted to be manipulated by a surgeon during implanting of the hair grafts. The elongate housing has a throughbore extending at least partway therealong from a first end thereof, and has a loading position adjacent to the throughbore for loading hair grafts into the instrument. A cutting device is affixed to the first end of the elongate housing by which the surgeon may make an incision in the patient's scalp, into which a hair graft is to be implanted. In the instrument, an implanting member is disposed axially movably within the throughbore of the elongate housing, and includes a forwardly projecting finger. The implanting member is movable from a first position in which the finger is positioned adjacent to the loading position so as to be able to load a hair graft, to a second position in which a loaded hair graft is bounded between the finger and the cutting device, and to a third position in which the finger extends beyond the cutting device.

First Embodiment

A first embodiment of the present invention is shown in FIG. 2, which is comprised of FIGS. 2A to 2F. Specifically, FIG. 2 shows operation of instrument 21 at various stages of a hair transplantation procedure, the details of which are described below.

As shown in FIG. 2, instrument 21 includes elongate housing 22 having throughbore 24 and loading position 26 adjacent to throughbore 24. Also included in instrument 21 are plunger 26, spring 27, compression washer 29, cutting device 30, which is affixed to end 25 of elongate housing 22, and implanting member 31, which is movably disposed within throughbore 24.

Elongate housing 22 is manipulable by a surgeon during implantation of hair grafts into patient's scalp 32. To this end, elongate housing 22 preferably has a tubular shape and a size which makes it easy to handle. A size of roughly 4 to 8 inches (≈10 to 20 centimeters) is preferred.

Elongate housing 22 includes throughbore 24, running at least partway therethrough from end 25. In this regard, FIG. 2 shows throughbore 24 running all the way through elongate housing 22. This configuration accommodates plunger 26, which may be actuated from the top of elongate housing 22 by, for example, a surgeon's thumb or index finger. As described in detail below, this actuation causes implanting member 31 to move within throughbore 24 relative to cutting device 30.

It should be noted that although the configuration of throughbore 24 shown in FIG. 2 is preferred, other configurations are possible. As will become evident below, the extent of throughbore 24 within elongate housing 22 is not critical. Thus, throughbore 24 could run only partway up elongate housing 22 from end 25. Such a configuration would support the use of a side-mounted mechanism (not shown), rather than a top-mounted plunger, to actuate implanting member 31.

FIG. 2 also shows loading position 26, into which individual hair grafts, such as graft 34, are loaded, follicle-side down. Loading position 26 is adjacent to throughbore 24 and may comprise a separately-identifiable slot within elongate housing 22, or it may simply be a position within throughbore 24 at which hair grafts are loaded, as shown in FIG. 2. In any event, loading position 26 should be positioned within a path of movement of implanting member 31 within elongate housing 22, so that implanting member 31 can pick up a hair graft loaded in loading position 26, as described in more detail below.

Hair grafts may be manually loaded into loading position 26, or they may be loaded automatically using an automatic loading mechanism. In preferred embodiments of the invention, an automatic loading mechanism is used and comprises either a circular or a linear magazine cartridge, which stores plural hair grafts in plural slots, and which loads the plural hair grafts sequentially from the magazine cartridge into loading position 26.

Figure 3:
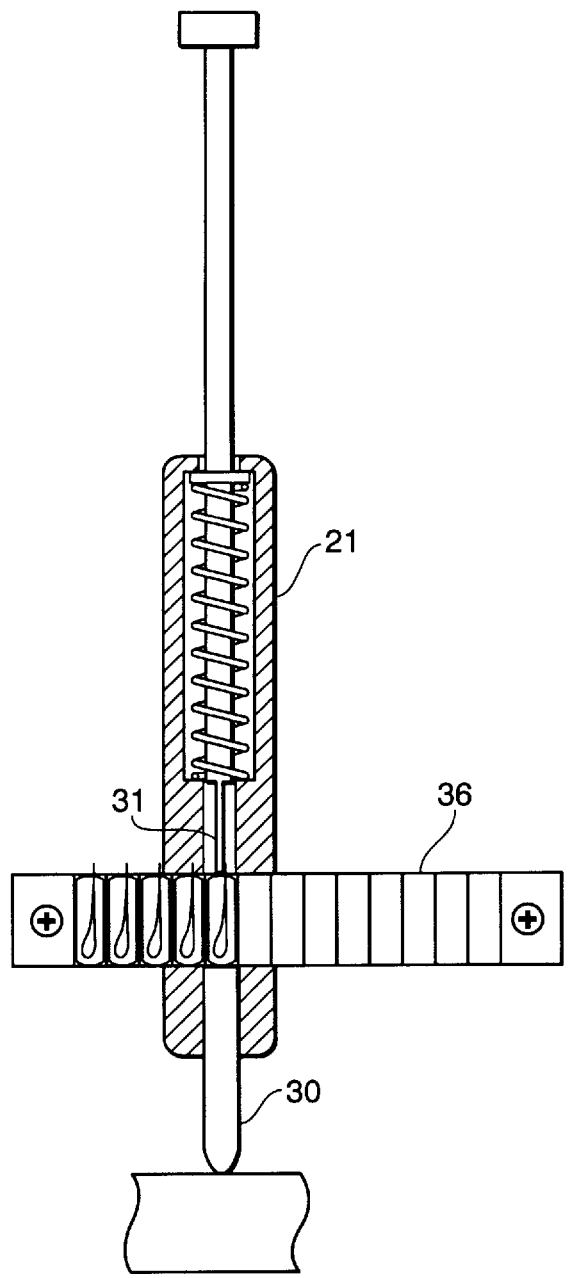
FIG. 3 shows a front view of the hair implanting instrument of the present invention, which includes a linear magazine cartridge for automatically loading hair grafts.
Figure 4:
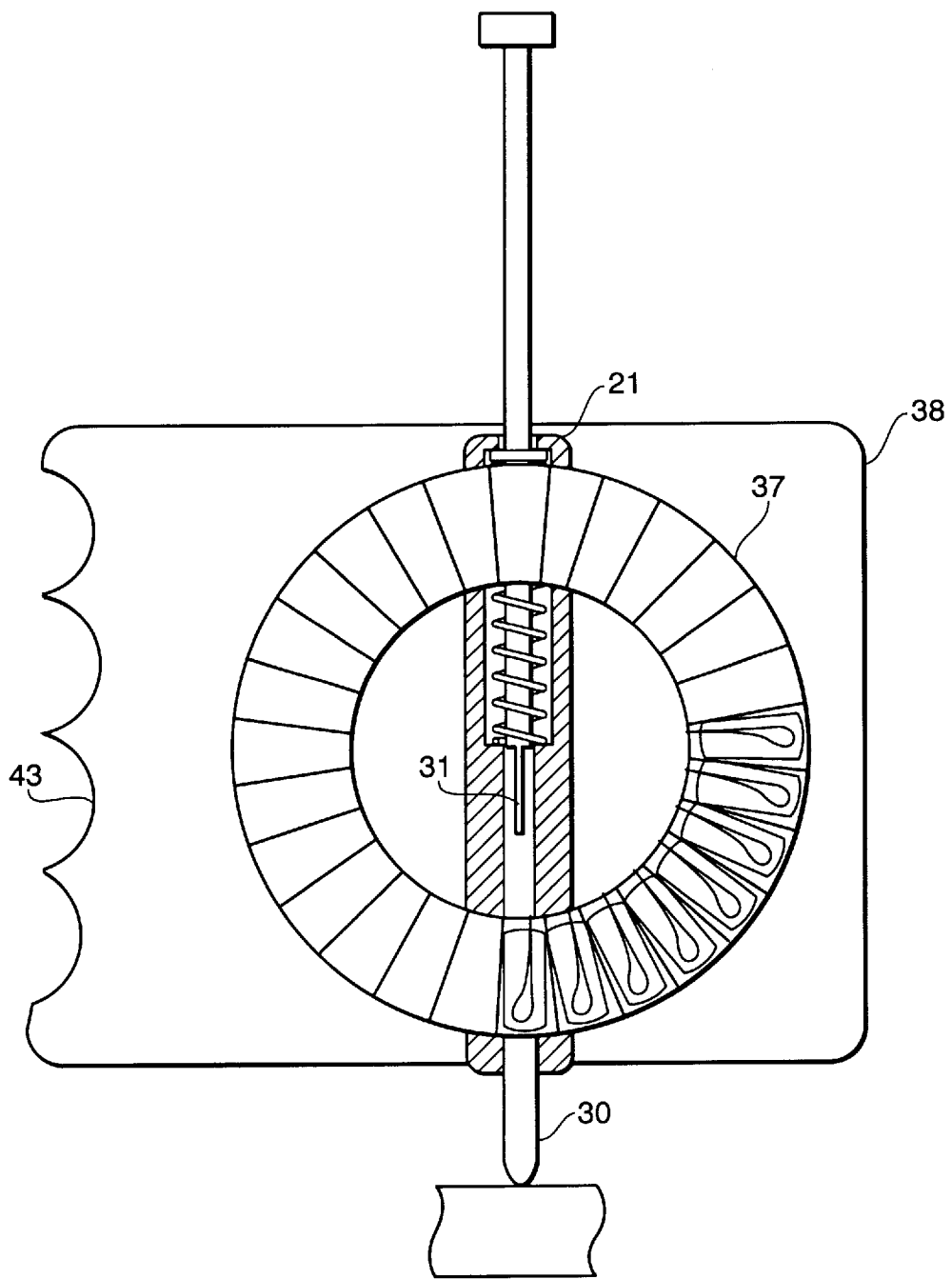
FIG. 4 shows a front view of the hair implanting instrument of the present invention which includes a circular magazine cartridge for automatically loading hair grafts.

FIGS. 3 and 4 show examples of linear and circular magazine cartridges 36 and 37, respectively, which can be used with instrument 21. Magazine cartridges 36 and 37 include plural slots, each of which stores a hair graft to be implanted. In preferred embodiments, the magazine cartridges are replaceable and the slots are reloadable. In addition, the magazine cartridges preferably advance automatically to a next slot each time a hair graft in a current slot is implanted, so as to permit implanting member 31 to access a new hair graft for implanting. Mechanisms for effecting such advancement are well known in the art and, therefore, will not be described in detail herein.

Cartridge 37 includes hand piece 38, which is mechanically attached to instrument 21. As shown, hand piece 38 includes grooves 43, which roughly accommodate a person's fingers, and which may be grasped by a surgeon during operation of instrument 21.

Returning to FIG. 2, cutting device 30 is used to make an incision in a patient's scalp, into which a hair graft is to be implanted. As shown, cutting device 30 is affixed to end 25 of elongate housing 22 and runs roughly parallel to throughbore 24. In the preferred embodiment of the invention, cutting device 30 comprises a flat blade, as shown in FIG. 2. Close-up front and side views, respectively, of a flat blade cutting device used in instrument 21 are shown in FIGS. 5A and 5B.

In this regard, although a flat blade is the preferred type of cutting device used in the present invention, other types of cutting devices may be used in lieu of a flat blade. Examples of these other cutting devices are shown in FIGS. 6A to 8B. Specifically, FIGS. 6A and 6B show front and side views, respectively, of a half-round needle which may be used as the cutting device. FIGS. 7A and 7B show front and side views, respectively, of a round needle which may be used as the cutting device. FIGS. 8A and 8B show front and side views, respectively, of a pointed (i.e., Nokor) needle which may be used as the cutting device. It should be noted that these figures merely present examples of different types of cutting devices which may be used in the present invention, and are not meant to be exhaustive.

Returning to FIG. 2, implanting member 31 is disposed axially within throughbore 24 of elongate housing 22. Implanting member 31 is movable within throughbore 24 relative to cutting device 30, as shown in the sequence depicted in FIG. 2, so as to move a hair graft from loading position 26 into incision 39 (see FIG. 2B) created by cutting device 30.

To this end, implanting member 31 is comprised of blunt end 40 and finger 41 projecting forwardly beyond blunt end 40. In this regard, finger 41 may project forwardly from blunt end 40, as shown in FIG. 2, or it may merely project forwardly beyond blunt end 40. An example of a finger which merely projects beyond, and not directly from, the blunt end is described below with respect to FIG. 15. Such a finger could be used in this embodiment of the invention.

Finger 41 preferably has a cross-sectional area which is less than that of blunt end 40, and a width which is less than that of blunt end 40. FIGS. 9A and 9B show side and front views, respectively, of a preferred embodiment of finger 41. Another embodiment of finger 41 is shown in FIGS. 10A and 10B. That is, FIGS. 10A and 10B show side and front views, respectively, of a finger having dimensions which are different from those shown in FIGS. 9A and 9B. The embodiment of finger 41 shown in FIGS. 9A and 9B is preferred over that shown in FIGS. 10A and 10B because it is more narrow. In this regard, a narrow finger is preferred because it reduces frictional drag on an implanted hair graft during withdrawal of the finger from the incision. This reduces the chances that the hair graft will inadvertently be pulled out of the incision during withdrawal of the finger, as described in more detail below.

Moreover, a narrow finger facilitates loading of a hair graft into implanting member 31. That is, as shown in FIG. 2B, during loading, finger 41 slides alongside hair graft 34 so that finger 41 is adjacent to hair graft 34 and so that blunt end 40 abuts the non-follicle end of the hair graft. In this regard, the more narrow that finger 41 is, the easier it is for finger 41 to slide alongside hair graft 34.

Finger 41 should have a length sufficient to penetrate a patient's scalp to the depth of patient's skull 44, as shown in FIG. 2. In this regard, finger 41 may either be longer or shorter than hair graft. Preferably, finger 41 is about 0.5 inches ($\approx 1$ centimeter) long. In addition, in preferred embodiments of the invention, at least part of finger 41 is made of polycarbonate steel, or a similar material which is highly flexible but which guards against breakage. By using a finger made from such a material, the invention reduces the chances that the finger will break off in the incision. It should be noted, however, that the finger can be made of any material, and need not necessarily include polycarbonate steel or other metal.

As shown in FIG. 2, implanting member 31 is movable from the position shown in FIG. 2A, in which finger 41 is not in contact with hair graft 34 in loading position 26, to the position shown in FIG. 2B, in which finger 41 is positioned adjacent to hair graft 34 in loading position 26. Implanting member 31 is then movable from the position shown in FIG. 2B to that shown in FIG. 2C, in which finger 41 and hair graft 34 open incision 39, and then to that shown in FIG. 2D, in which both finger 41 and cutting device 30 are inside incision 39, and in which hair graft 34 is bounded between finger 41 and cutting device 30. Further, as shown in FIGS. 2D and 2E, implanting member 31 is movable from the position shown in FIG. 2D to that shown in FIGS. 2E and 2F, in which finger 41 extends beyond cutting device 30. A detailed description of the relevance of implanting member 31's movement between the positions shown in FIGS. 2A to 2F is described in more detail below.

Also included within instrument 21 are spring 27 and compression washer 29. These elements are used to control movement of implanting member 31 within throughbore 24. That is, as shown in FIGS. 2B to 2E, compression washer 29 is physically connected to plunger 26 and moves in synchronism therewith. Thus, when plunger 26 is actuated, compression washer 29 causes spring 27 to compress, thereby providing a fluid motion of implanting member 31 inside throughbore 24. Once pressure is removed from plunger 26, spring 27 expands, thereby causing implanting member 31 to retract to the position shown in FIG. 2A.

Figure 11:
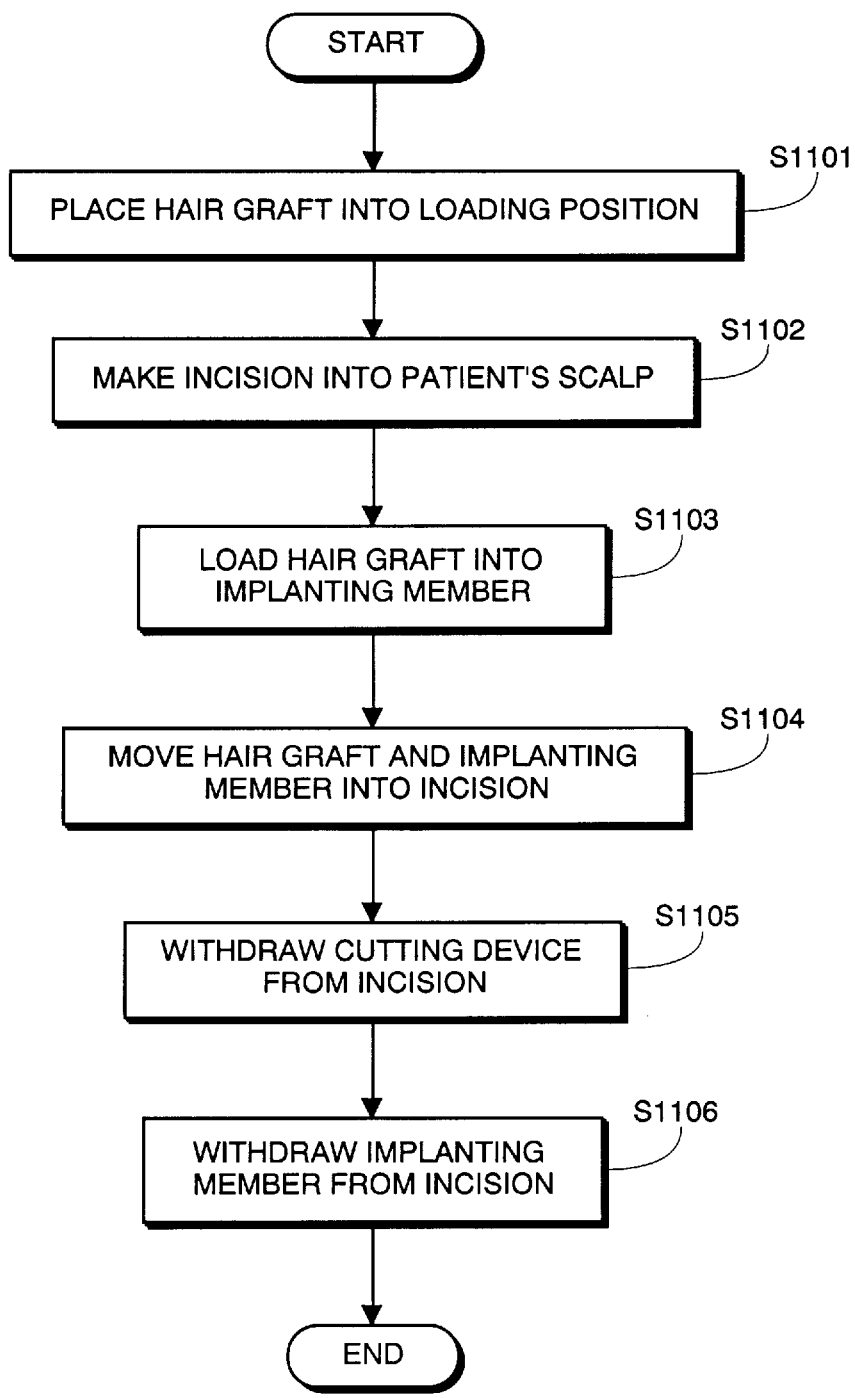
FIG. 11 is a flow chart depicting steps in a hair transplantation procedure using the first, second and fourth embodiments of the hair implanting instrument of the present invention.

FIG. 11 is a flow chart which explains the hair transplantation procedure depicted graphically in FIG. 2. More specifically, as shown in FIGS. 2A and 11, in step S1101, hair graft 34 is placed into loading position 26. In the embodiment of the invention shown in FIG. 2, loading position 26 comprises a particular area of throughbore 24. However, as noted above, loading position 26 can comprise a separately-identifiable slot. In any event, once hair graft 34 is placed in loading position 26, flow proceeds to step S1102.

In step S1102, a surgeon makes incision 39 into patient's scalp 32 using cutting device 30, as shown in FIG. 2B. Since hair grows out of the scalp at an angle, the incision is made, and the hair grafts are implanted, at an angle relative to the scalp (e.g., angle 49 shown in FIG. 2B) in order to approximate natural hair growth. Preferably, this angle is around 60°, but any angle may be chosen, depending upon the patient, the surgeon, and other relevant factors.

In preferred embodiments of the invention, cutting device 30 is advanced in the incision until it reaches patient's skull 44, as shown in FIG. 2B. While an incision of this depth is preferred, the incision need not reach the patient's skull, and the depth thereof may be set by the surgeon, as desired, based on a number of factors, such as hair graft size, scalp thickness, etc. Additionally, the size, e.g., the width of the incision, depends primarily on the size of the cutting device used, and may be varied as desired.

FIG. 2B also depicts step S1103, which may or may not be performed at the same time as step S1102. In step S1103, hair graft 34 is loaded into implanting member 31. As shown in the figure, and as described above, implanting member 31 moves downwardly in response to force applied to plunger 26, so that finger 41 slides alongside and adjacent to hair graft 34 in loading position 26, and so that blunt end 40 abuts the non-follicle end of hair graft 34. In this configuration, hair graft 34 is bounded by finger 41 and the inner wall of throughbore 24.

Figure 2C:
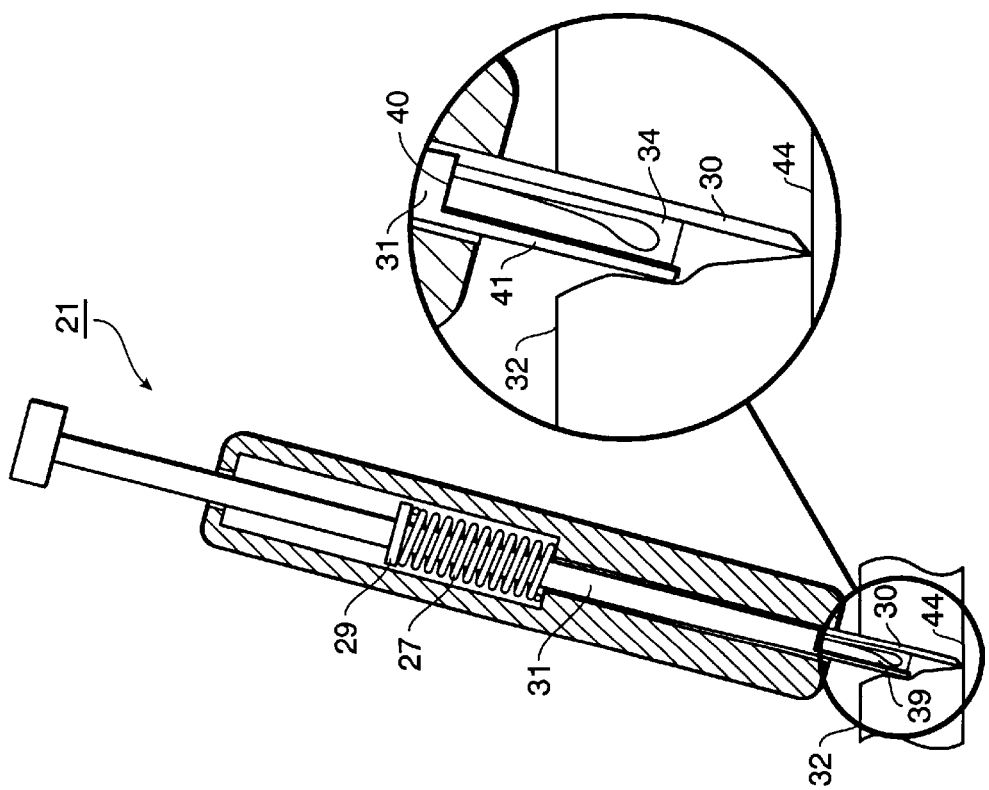

Next, in step S1104, implanting member 31 moves hair graft 34 and finger 41 into incision 39, as shown in FIGS. 2C and 2D. That is, FIG. 2C shows hair graft 34 and finger 41 moving into incision 39. As shown in that figure, during this movement, finger 34 "opens" incision 39 so that incision 39 is able to receive hair graft 34. FIG. 2D, on the other hand, shows the final results of the motion, i.e., finger 41 and hair graft 34 inside of incision 39.

In step S1104, finger 41 is moved into contact with patient's skull 44. This facilitates withdrawal of cutting device 30 from incision 39 as described in more detail below.

In this regard, frictional force between finger 41 and hair graft 34 creates a downward dragging force, which may be used to move hair graft 34 down throughbore 24 and into incision 39. Finger 41 shields at least part of hair graft 34 during this movement. Thus, in step S1104, movement of hair graft 34 into incision 39 is accomplished by (1) only pushing using blunt end 40, (2) only dragging via finger 41, or (3) both pushing using blunt end 40 and dragging using finger 41.

With regard to the dragging described above, hair graft 34 is preferably wet with saline and plasma. This causes hair graft 34 to "bond", via friction, to adjacent finger 41. The "bonding" enables finger 41 also to drag hair graft 34 downward in the direction of arrow 33 shown in FIG. 2B, while hair graft 34 is also being pushed by blunt end 40. As a result of this additional dragging, the amount of pushing required to move hair graft 34 into incision 39 is reduced.

In incision 39, hair graft 34 is bounded by finger 41 and cutting device 30, as shown in FIG. 2D, so that a protective sheath is created at least part way around hair graft 34. This is advantageous since, as noted above, excessive pressure applied to a hair graft can cause damage to the hair graft and/or cause the hair graft to deform. The protective sheath provided by finger 41 and cutting device 30 helps to maintain the hair graft's shape, and therefore reduces deformation and/or damage caused by pushing the hair graft into the incision. In addition, since the force applied to hair graft 34 includes a drag component provided by finger 41, the amount of pressure required to push hair graft 34 into incision 39 is reduced, thereby reducing the chances that hair graft 34 will be damaged and/or deformed during implanting.

Figure 2F:
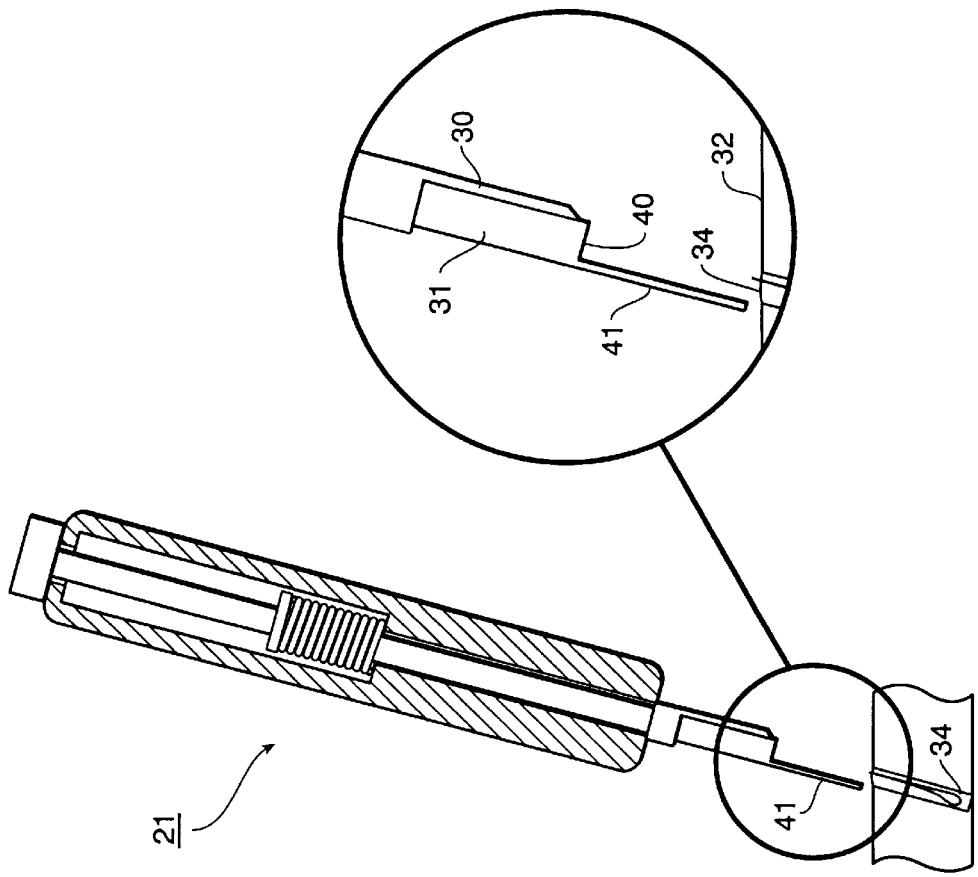
Figure 2E:
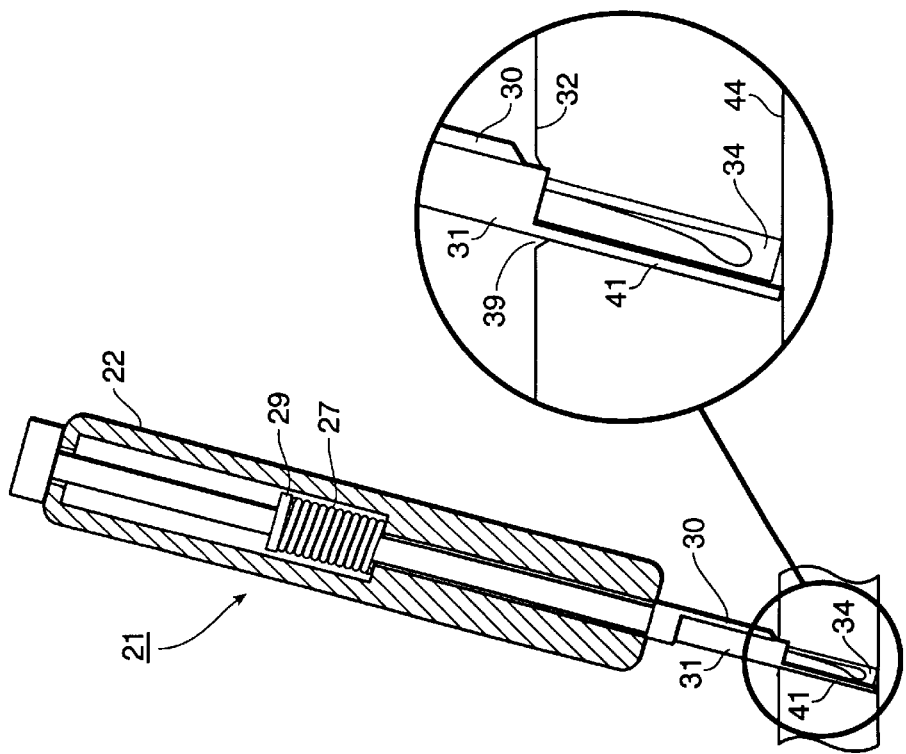

FIG. 2E depicts the next step in the hair transplantation procedure. More specifically, FIG. 2E shows step S1105, in which cutting device 30 has been withdrawn from incision 39. Withdrawal of cutting device 30 from incision 39 is performed as follows.

In this regard, as shown in FIG. 2D, in preceding step S1104, both finger 41 and cutting device 30 are in contact with patient's skull 44. However, as also shown in FIG. 2D, implanting member 31 has not been fully advanced. That is, compression washer 29 has not fully compressed spring 27, nor has plunger 26 reached contact with top 28 of elongate housing 22. Thus, additional advancement of implanting member 31 is possible from the position shown in FIG. 2D.

However, while additional advancement of implanting member 31, and thus finger 41, is possible, patient's skull 44 prevents finger 41 from advancing further. Accordingly, when additional force is applied to implanting member 31 via plunger 26, that additional force does not advance finger 41 forwardly. Rather, since finger 41 remains stationary against skull 44, the additional force is transmitted to elongate housing 22. The transmitted force is opposite to that applied to finger 41 and, as a result, causes elongate housing 22, and thus cutting device 30, to move upwardly. Thus, cutting device 30 withdraws from incision 39, leaving both finger 41 and hair graft 34 in the incision. This is shown in FIG. 2E.

In the foregoing manner, instrument 21 is able to withdraw cutting device 30 from patient's scalp 32 by applying pressure to the patient's skull rather than to the scalp. In fact, the only real pressure applied to the patient's scalp during a transplantation procedure using instrument 21 is caused by skin displacement during insertion of cutting device 30, finger 41, and/or hair graft 34. Since this pressure is relatively minor, it has little or no effect on previously-implanted, neighboring hair grafts. Accordingly, instrument 21 is able to withdraw cutting device 30 from incision 39 without significantly adversely affecting neighboring implanted hair grafts.

During withdrawal of cutting device 30 from the incision, friction between finger 41 and hair graft 34 causes hair graft 34 to remain in the incision, rather than pulling out along with cutting device 30. In addition, surface tension created by fluid in the incision and a vacuum created during implantation also aids in maintaining hair graft 34 in the incision during withdrawal of cutting device 30. Consequently, as noted above, finger 41 may be significantly narrower than cutting device 30, since frictional forces in addition to those created by finger 41 will act to hold hair graft 34 in incision 39.

Next, in step S1106 shown in FIG. 2F, finger 41 of implanting member 31 is withdrawn from incision 39, leaving hair graft 34 in the incision. This is accomplished by manually pulling instrument 21 out of the incision. Since, as noted above, finger 41 is relatively narrow, less frictional force is created between finger 41 and the hair graft in incision 39 than between the hair graft and cutting device 30. Accordingly, surface tension created by fluid in the incision and a vacuum created during implantation generally are sufficient to maintain hair graft 34 in the incision during withdrawal of finger 41.

Thus, as shown in FIG. 2F, hair graft 34 is left in patient's scalp 32. The procedure then ends for hair graft 34. Thereafter, it is repeated for other hair grafts in other areas of the patient's scalp.

Second Embodiment

A second embodiment of the invention is shown in FIG. 12, comprised of FIGS. 12A to 12G. As shown, the second embodiment includes elements which are similar to those shown in the first embodiment. For the sake of brevity, these elements, to the extent that they are the same as those shown in the first embodiment, will not be described in detail.

It should be noted, however, that the elements of the second embodiment can comprise any of the various elements described above with respect to the first embodiment. For example, the cutting device in this embodiment can comprise any of the cutting devices shown in FIGS. 5a to 8B. Likewise, the second embodiment can include either of the magazine cartridges shown in FIGS. 3 and 4.

In brief, in the second embodiment, the throughbore in the elongate housing includes at least one narrow segment and a wide segment which is adjacent to the loading position. The finger is fabricated from a springy material and is spring-loaded at least in the narrow segments of the throughbore. Thus, the finger roughly conforms to the narrow segment of the throughbore, and expands when it reaches the wide segment. The wide segment of the throughbore terminates in a camber, which includes an inclined surface capable of guiding the finger from the wide segment of the throughbore into the narrow segment of the throughbore. Preferably, the camber is gradually sloped downwardly from the wide segment to the narrow segment.

The tip of the finger, or other areas thereof, may be curved relative to an axis of the throughbore. As was the case with the first embodiment described above, the finger may be longer or shorter than a hair graft to be implanted. Thus, when the finger is both curved and shorter than the hair graft to be implanted, the finger pinches the hair graft against an inner wall of the throughbore as shown, for example, in FIG. 12C. On the other hand, in a case where the finger is both curved and longer than the hair graft to be implanted, the curved portion of the finger, such as the tip, provides additional protection for the hair graft during implantation. An example of such a case is described below with respect to FIG. 12G.

As was the case with respect to FIG. 2, FIG. 12 shows operation of the second embodiment of the invention, namely instrument 50, during stages of a hair transplantation procedure. As shown, in this embodiment, throughbore 51 includes narrow segments 52 and 54, which need not have the same cross-sectional area, and wide segment 56, which has a cross-sectional area greater than that of the narrow segments. Wide segment 56 is positioned adjacent to loading position 57, and facilitates hair graft loading as described below.

In this embodiment, finger 59 is fabricated from a springy material and is spring-loaded at least inside of narrow segments 52 and 54. In wide segment 56, finger 59 expands, although it may still be spring-loaded, only less so than in the narrow segments. This feature of the invention is advantageous because it facilitates loading of hair grafts, as described in more detail below.

Additionally, as shown in FIG. 12, in this embodiment of the invention, tip 58 of finger 59 is preferably curved. Although this is the preferred configuration of finger 59, it should be noted that other portions of finger 59 may be curved. Alternatively, finger 59 may be straight, as shown above with respect to FIG. 2.

Next, at an end of loading position 57, instrument 50 includes camber 60, which guides finger 59 from wide segment 56 into narrow segment 54. In doing so, camber 60 forces finger 59 into narrow segment 54. In a preferred embodiment, camber 60 gradually slopes downwardly from wide segment 56 to narrow segment 54. Other configurations of camber 60 are possible, however.

Figures 12C, 12D:
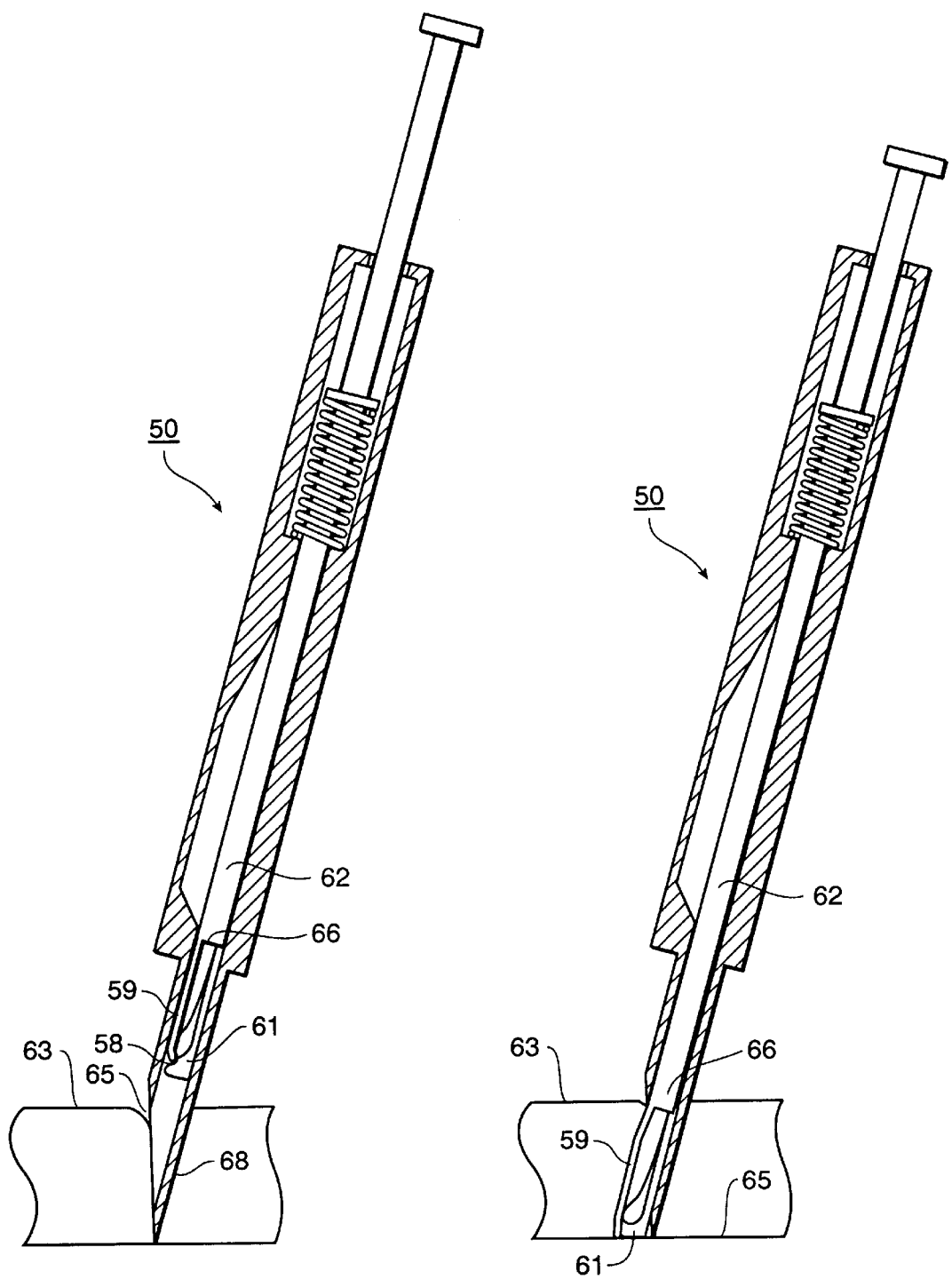
FIG. 12, comprised of FIGS. 12A, 12B, 12C, 12D, 12E, 12F and 12G, shows side views of a second embodiment of the hair implanting instrument of the present invention during various stages of a hair transplantation procedure.
Figure 12E:
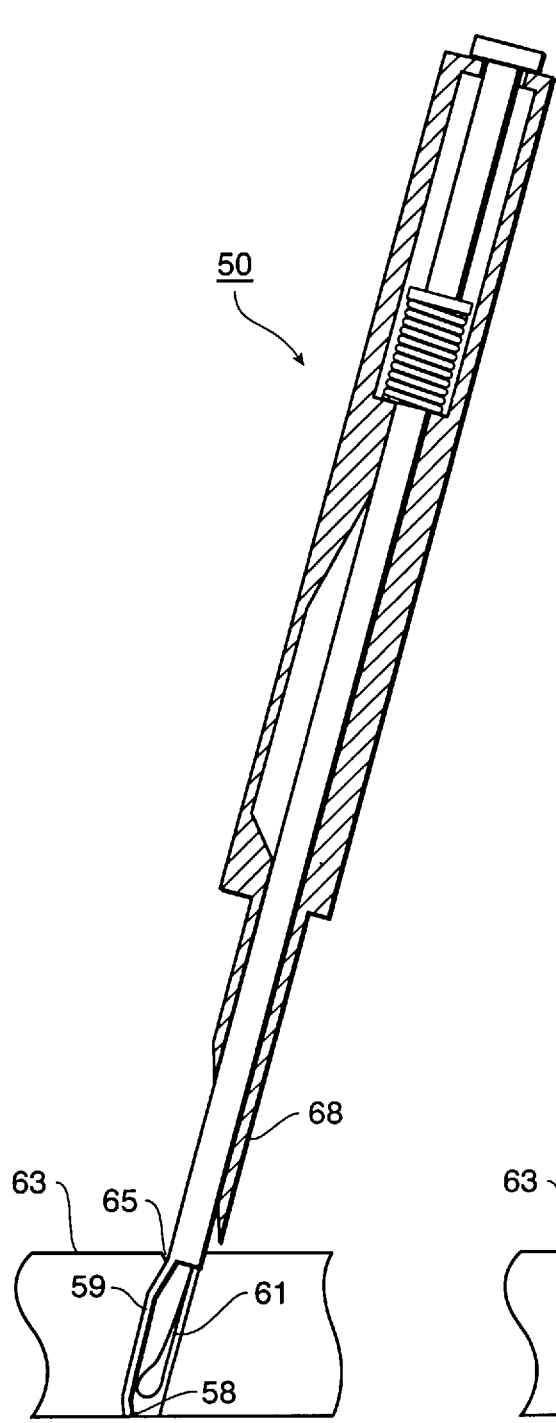
Figure 12F:
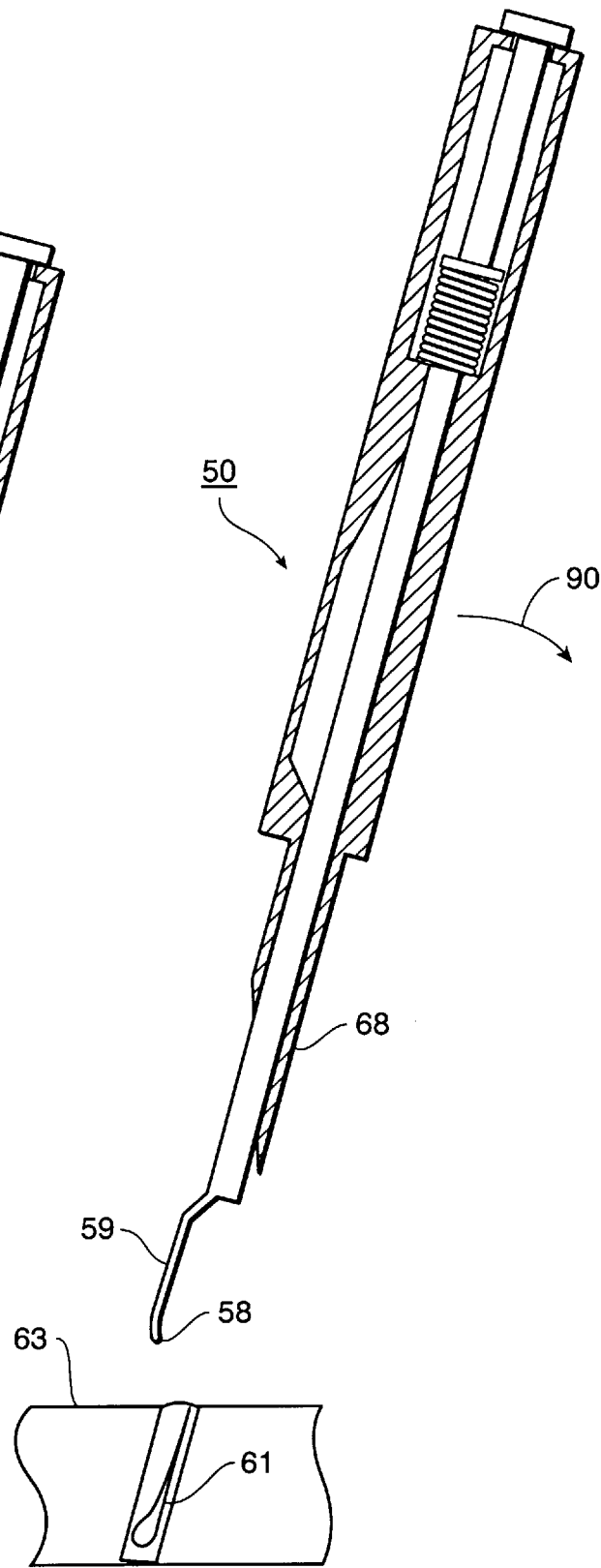
Figure 12G:
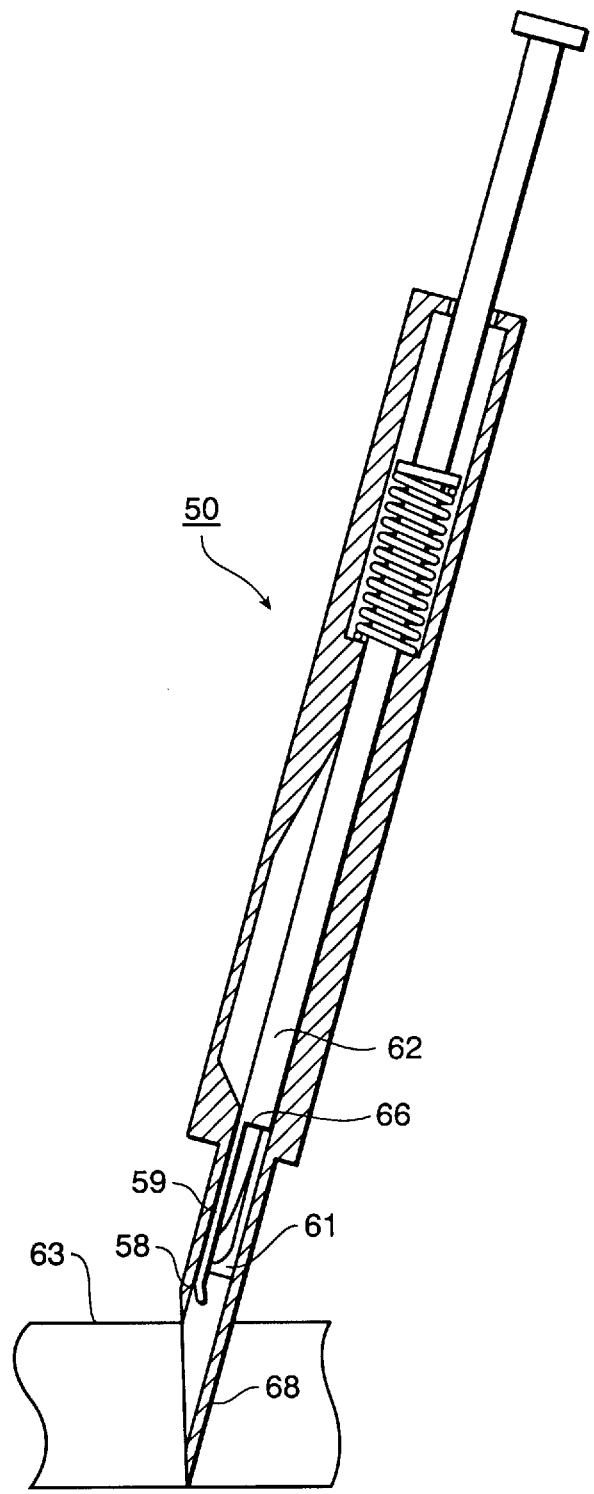

In a case where finger 59 is shorter than the hair graft being implanted, as is the case in the example show in FIG. 12C, finger 59 pinches hair graft 61. This pinching action aids in the movement of hair graft 61 into the incision, as described in more detail below. On the other hand, where finger 59 is longer than the hair graft being implanted, as noted above, finger 59 acts as additional protection for the hair graft during implantation, as shown in FIG. 12G.

Operation of instrument 50 will now be described with respect to the flowchart shown in FIG. 11. In this regard, in step S1101, shown graphically in FIG. 12A, a hair graft is placed into loading position 57, as was the case in the first embodiment of the invention described above. Thereafter, in step S1102, shown graphically in FIG. 12B, cutting device 68, which in this case is a round needle-type cutting device, makes incision 65 into patient's scalp 63 in a manner identical to that described in the first embodiment.

In step S1103, also shown graphically in FIG. 12B, hair graft 61 is loaded into implanting member 62. In this embodiment, unlike in the first embodiment, finger 59 is fabricated from a springy material such that it is spring-loaded at least within narrow segment 52 of throughbore 51 prior to step S1103 (see FIG. 12A). Thus, when finger 59 reaches wide segment 56 at loading position 57, finger 59 expands (see FIG. 12B). This facilitates loading of the hair graft in step S1103, since contact between hair graft 61 and finger 59 at loading position 57 is reduced as finger 59 slides adjacent to hair graft 61. That is, since finger 59 expands in accordance with wide segment 56, frictional force between finger 59 and hair graft 61 during loading is reduced and may, if wide segment 56 is sufficiently wide as is the case in FIG. 12B, eliminate contact between the hair graft and the finger during loading. Consequently, the chances that hair graft 61 will prematurely advance within throughbore 51 during loading are also reduced.

As noted above, finger 59 expands within wide segment 56. In this regard, within wide segment 56, finger 59 may still be compressed, just less so than within the narrow segments. In such cases, frictional force would still be reduced between the hair graft and the finger.

Figure 15:
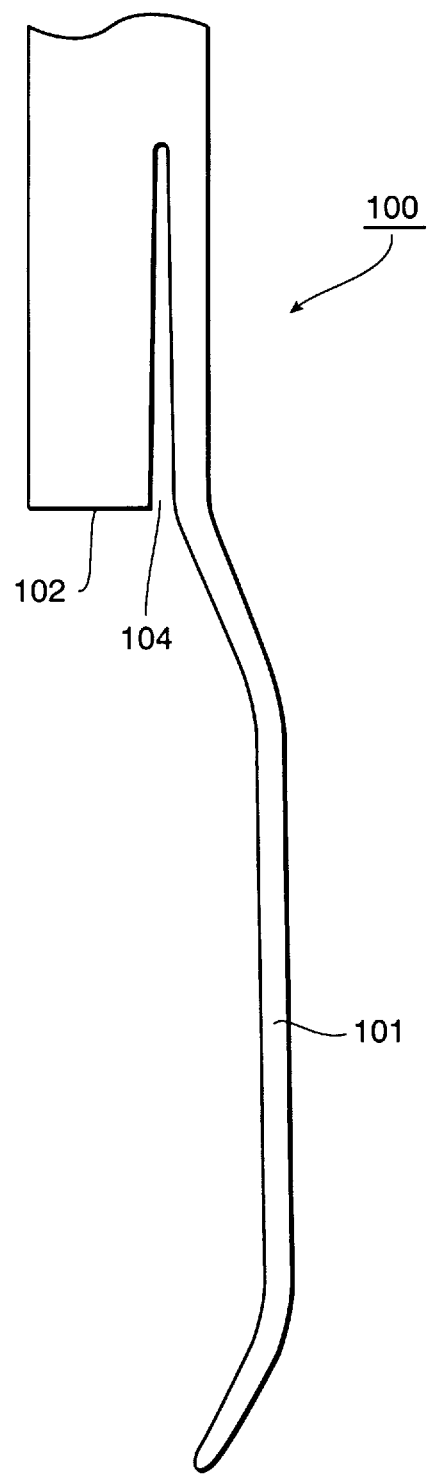
FIG. 15 shows a side view of an alternative embodiment of the implanting member which may be used in the present invention.

An alternative embodiment of an implanting member which may be used in any embodiment of the invention is shown in FIG. 15. More specifically, in FIG. 15, like in foregoing implanting member 62 shown in FIG. 12, implanting member 100 includes both a finger and a blunt end. However, as shown in FIG. 15, finger 101 is connected to implanting member 100 downstream from blunt end 102 and is separated therefrom by slit 104. This configuration facilitates compression of the finger within narrow segments 52 and 54, and expanding of the finger within wide segment 56, as described above.

Returning to FIG. 11, in step S1103, camber 60 guides finger 59 from wide segment 56 into narrow segment 54. In a case where finger 59 is shorter than the hair graft, such as in FIG. 12C, this causes curved tip 58 of finger 59 to pinch the hair graft against an inner wall of the throughbore. This pinching action facilitates movement of the hair graft from throughbore 51 into the incision. That is, by pinching the hair graft in this manner, implanting member 62 is able to drag the hair graft into the incision using finger 59. The dragging motion can be exclusive of, but is preferably in addition to, the pushing provided by blunt end 66 of implanting member 62.

In addition, by pinching the hair graft with finger 59 in the manner described above, it is possible to fit the hair graft into a relatively small incision. That is, the pinching action reduces the portion of the hair graft which first enters into the incision, thereby making it easier to fit the hair graft into the incision. This allows for placement of relatively small hair grafts, such as follicular grafts, much more efficiently than conventional instruments which do not pinch the hair graft.

Moreover, since the hair graft is made primarily of skin and fat, it is inherently stretchable. Consequently, when the hair graft is dragged into the incision via the above-described pinching action, it is elongated. As a result, the width of the hair graft is reduced, also making it easier to fit the hair graft into a smaller incision A case where finger 59 is longer than the hair graft is shown in FIG. 12G, which depicts instrument 50 in the same operational position as in FIG. 12C, thus making FIGS. 12C and 12G interchangeable in the process depicted in FIG. 12. In the case shown in FIG. 12G, curved tip 58 of finger 59 extends beyond the follicle end of hair graft 61 and, as a result, provides additional protection for hair graft 61 during implantation, but does not pinch hair graft 61.

Following step S1103, flow proceeds to step S1104. In step S1104, which is shown graphically in FIG. 12D, implanting member 62 moves hair graft 61 and finger 59 into the incision in scalp 63 such that finger 59 contacts skull 65. In doing so, as was the case with respect to FIG. 2, finger 59 opens the incision so that the hair graft can be implanted therein. The step of opening the incision is similar to that depicted above in the first embodiment and is, therefore, not depicted graphically.

Flow then proceeds to steps S1105 and S1106, which are similar to those described above for the first embodiment. For completeness, FIGS. 12E and 12F are provided, which graphically depict steps S1105 and S1106, respectively. That is, FIG. 12E shows step S1105, in which cutting device 68 is withdrawn from incision 65, and FIG. 12F shows step S1106, in which implanting member 62 is withdrawn from the incision, leaving the hair graft implanted in scalp 63.

In this regard, in step S1106, implanting member 62 is preferably withdrawn in a slightly curved direction, roughly along the lines of arrow 90 in FIG. 12F. Implanting member 62 is withdrawn in this manner so as to reduce the chances that curved tip 58 of finger 59 will significantly pull hair graft 61 out of the incision during withdrawal of finger 59.

Following step S1106, the process is repeated to implant additional hair grafts in other areas of the patient's scalp.

Third Embodiment

A third embodiment of the invention is shown in FIG. 13. In this regard, FIG. 13 depicts instrument 70, which includes holding member 71 (see FIG. 13E) described below. Only those portions of the third embodiment which are different from the first embodiment are depicted in FIG. 13. In addition, detailed descriptions of elements of the third embodiment which are identical to those of the first embodiment are omitted for the sake of brevity.

In this regard, it should be noted that the elements that comprise the third embodiment can include any of the various elements described above with respect to the first and second embodiments. For example, the cutting device in the third embodiment can comprise any of the cutting devices shown in FIGS. 5a to 8B; either of the magazine cartridges shown in FIGS. 3 and 4 can be included in the third embodiment; the finger can be either straight or curved (e.g., as shown in FIG. 15), spring-loaded or rigid, or longer or shorter than loaded hair grafts; the throughbore can include wide and narrow segments or be all one size; etc.

In brief, the third embodiment of the invention has an implanting member which includes a throughbore at least partway therethrough, and a holding member disposed within the throughbore and movable relative to the implanting member's finger. In this regard, the holding member is movable from an unextended position, in which it extends to less than a length of the finger, to an extended position, in which it extends to greater than a length of the finger.

Thus, as shown in FIG. 13, implanting member 72 includes throughbore 75 at least partway therethrough into which holding member 71 is disposed. Holding member 71 fits within the throughbore and is capable of moving therein relative to finger 76 as shown, for example, in FIGS. 13D and 13E.

In this regard, a variety of means can be used to control movement of holding member 71 within the throughbore. For example, a latching mechanism (not shown) could latch holding member 71 until holding member 71 reaches scalp 77. Thereafter, the latch could be released, allowing holding member 71 to remain extended even after both cutting device 79 and finger 76 have been withdrawn. Following the implanting process, holding member 71 could be withdrawn and relatched.

In preferred embodiments of the invention, holding member 71 includes foot 80 affixed to an end thereof. Foot 80 is preferably made of a sponge-like material which is compressible and expandable. Use of a sponge-like material is advantageous because it reduces the chances that a hair graft in contact with foot 80 will be damaged and/or deformed due to pressure applied thereby. In addition, because foot 80 is made of a sponge-like material, it is able to retract within the throughbore, if necessary.

Figure 14:
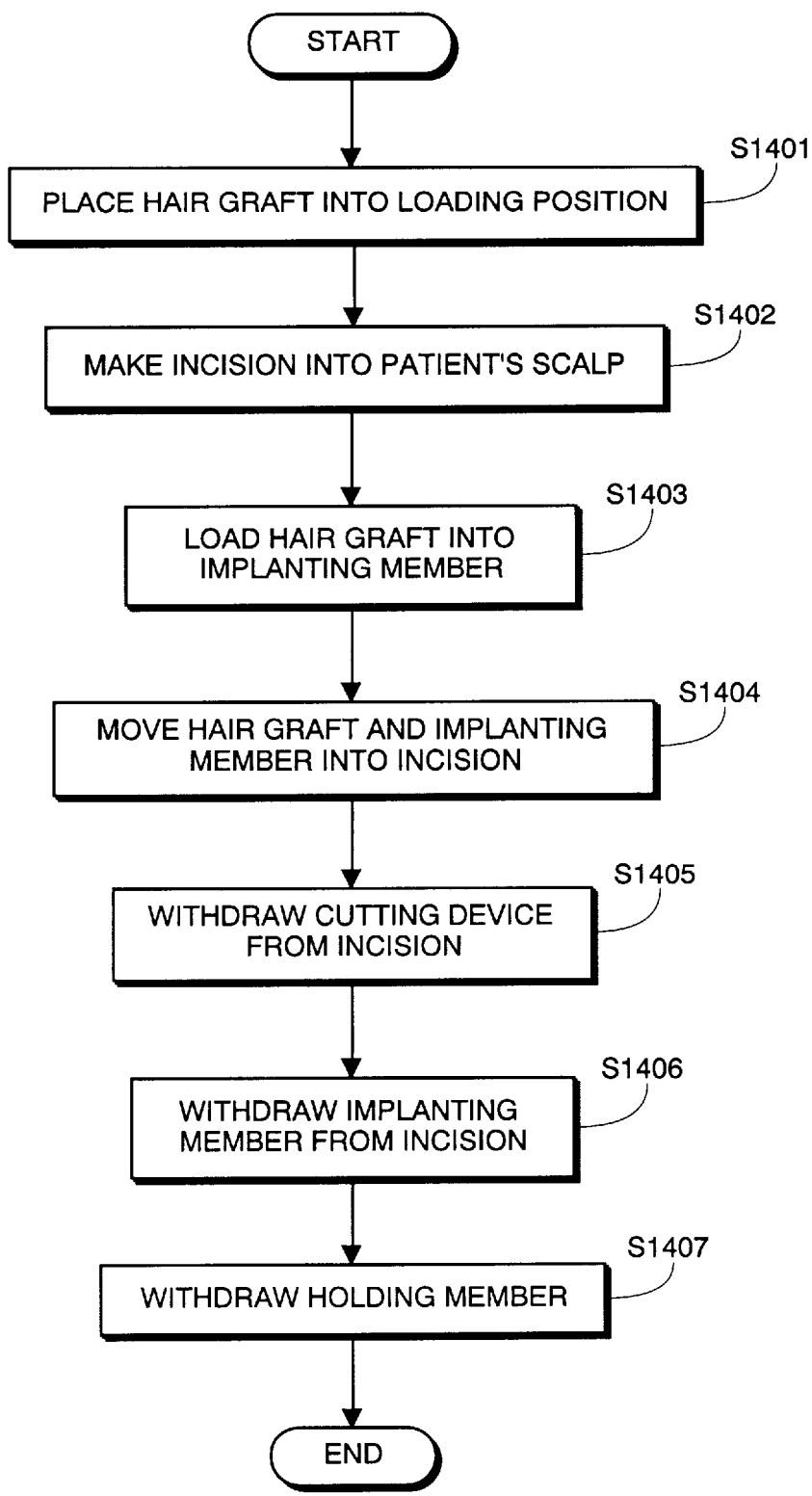
FIG. 14 is a flow chart depicting steps in a hair transplantation procedure using the third embodiment of the hair implanting instrument of the present invention.

FIG. 14 shows a flow chart which explains the hair transplantation procedure depicted graphically in FIG. 13. In this regard, steps S1401 to S1403, depicted graphically in FIGS. 13A and 13B, are identical to steps S1101 to S1103 described above with respect to FIG. 11. Accordingly, a detailed description thereof will be omitted here for the sake of brevity.

Thus, following step S1403, in step S1404 implanting member 72 moves hair graft 82 into an incision created by cutting device 79 such that the hair graft is bounded by cutting device 79 and finger 76, and such that finger 76 is in contact with the patient's skull (see FIG. 13C). In that step, once hair graft 82 is moved into the incision, holding member 71 is preferably released. That is, holding member 71 is released so that it can remain in contact with the non-follicle end of hair graft 82, as shown in FIGS. 13C to 13E. It should be noted, however, that holding member 71 could alternatively be released following steps S1405 or S1406.

In this regard, following step S1404, cutting device 79 is withdrawn from the incision in step S1405 (see FIG. 13D) followed, in step S1406, by finger 76 (see FIG. 13E). Withdrawal of cutting device 79 and finger 76 are performed in the same manner as described above with respect to the first and second embodiments. In this third embodiment, however, unlike in the first two embodiments described above, following step S1406, holding member 71, specifically foot 80, remains in contact with the non-follicle end of hair graft 82 in the incision, as shown, for example, in FIG. 13E. In this manner, holding member 71 reduces the chances that the hair graft will be withdrawn from the incision during withdrawal of cutting device 79 and finger 76.

Thereafter, in step S1407, holding member 71, including foot 80, is withdrawn from hair graft 82, as shown in FIG. 13F. The above process is then repeated for additional hair grafts in other areas of the scalp.

Fourth Embodiment

Figure 16A:
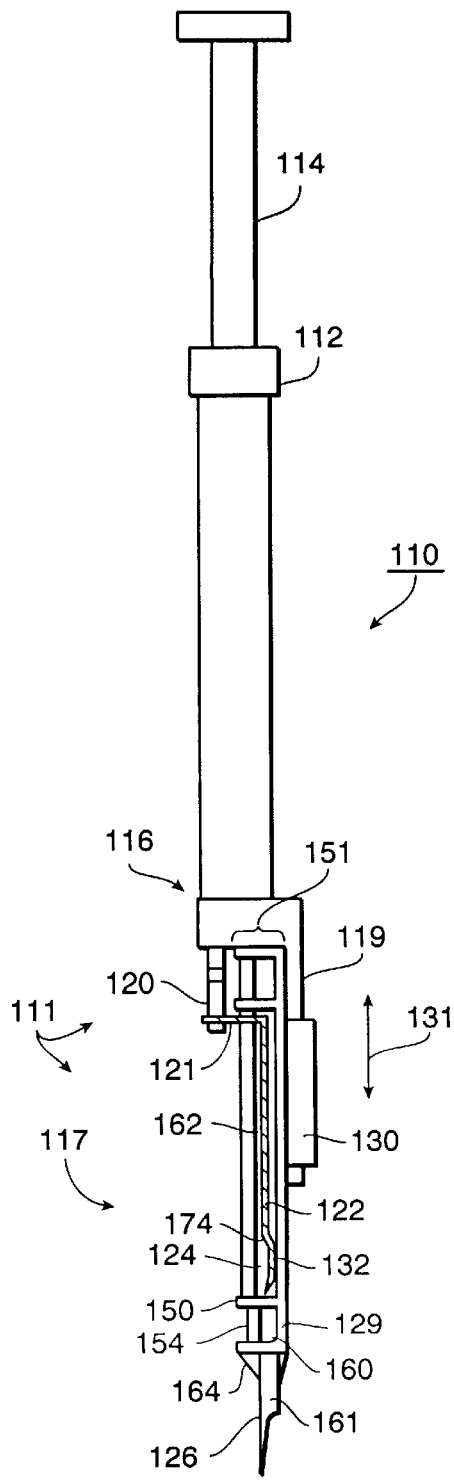
FIG. 16, comprised of FIGS. 16A and 16B, shows side and front views, respectively, of a fourth embodiment of the hair implanting instrument of the present invention.
Figure 16B:
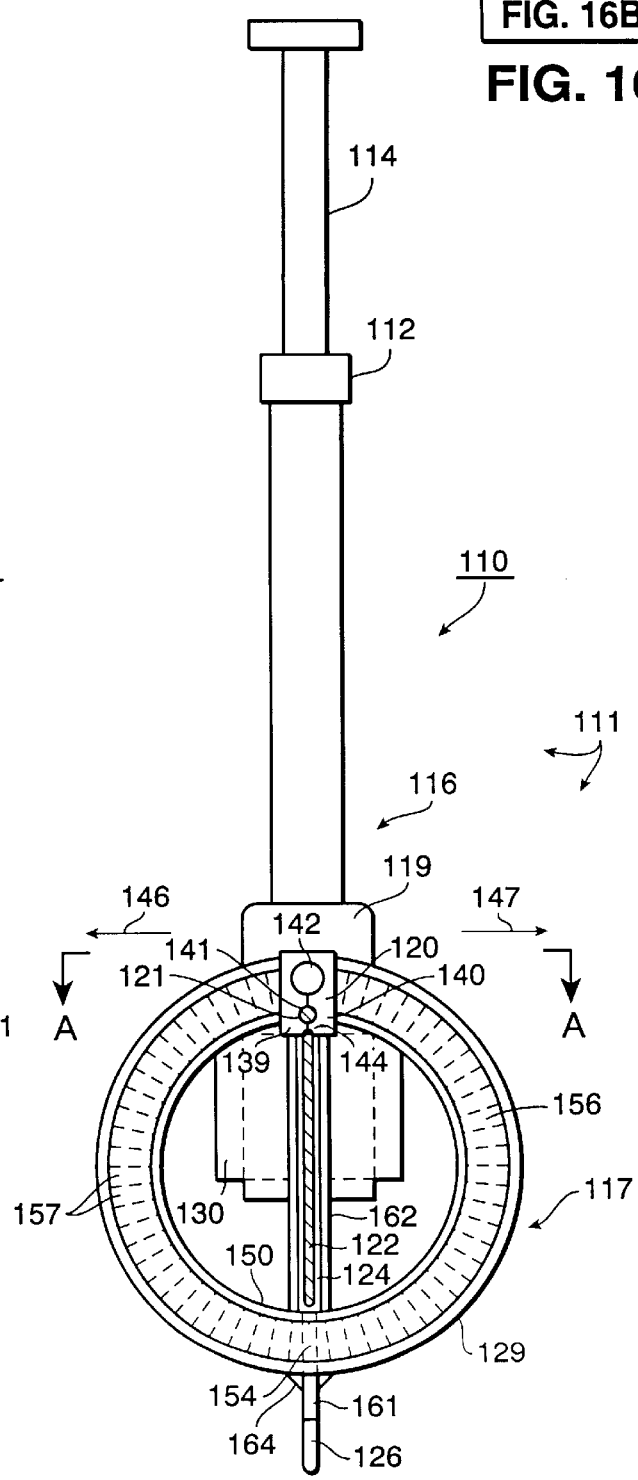

Front and side views, respectively, of a fourth embodiment of the present invention are shown in FIG. 16, which is comprised of FIGS. 16A and 16B. In this regard, FIG. 16A is a side view of instrument 110 shown in FIG. 16B, in which a cross-section has been taken along line A—A.

At this point, it should be noted that the elements that comprise the fourth embodiment of the invention can include any of the various elements described above with respect to the first, second and third embodiments. For example, the cutting device in the fourth embodiment can comprise any of the cutting devices shown in FIGS. 5a to 8B; the finger can be either straight or curved (e.g., as shown in FIG. 15), spring-loaded or rigid, or longer or shorter than loaded hair grafts; etc. However, features of the fourth embodiment which are identical to corresponding features in the first to third embodiments will not be described in detail.

As shown in FIG. 16, instrument 110 includes elongate housing 111 having top end 112, and plunger 114 which, when depressed, contacts top end 112. Elongate housing 111 includes both upper portion 116 and lower portion 117. Upper portion 116 includes springs, a throughbore, and a compression washer therein, which are substantially identical to those shown and described in FIGS. 2 and 12. Accordingly, a detailed description and depiction of these elements is omitted for the sake of brevity. Upper portion 116 also includes tongue 119, described in more detail below, which connects upper portion 116 to lower portion 117.

Also included in upper portion 116 is grabber 120. Grabber 120 is movably disposed within the throughbore of upper portion 116, and movement of grabber 120 is controlled by plunger 114. In this regard, grabber 120 can retract within upper portion 116, in order to permit insertion of a circular cartridge with loaded hair grafts (described below), and can extend along lower portion, as shown in FIG. 17. Grabber 120 holds elbow 121 of implanting member 122, both of which are shown in FIG. 16, for the purpose described below.

Lower portion 117 of elongate housing 111 includes throughbore 124 which runs at least partway up from cutting device 126, and into which implanting member 122 is disposed axially. In this regard, in this embodiment of the invention, at least a portion of throughbore 124 is exposed so that elbow 121 can move therein A detailed description of the reason for this is given below.

Lower portion 117 also includes circular magazine 129, into which a circular cartridge containing loaded hair grafts may be inserted. Affixed to circular magazine 129 via screws or the like is connector 130, into which tongue 119, described above, slides, in order to connect upper portion 116 of elongate housing 111 to lower portion 117 of elongate housing 111.

In preferred embodiments of the invention, upper portion 116 is separable from lower portion 117 by pulling upper portion 116 and lower portion 117 in the directions of arrow 131, shown in FIG. 16A. This motion releases tongue 119 from connector 130, thereby separating the upper and lower portions. Of course, in order to separate the portions, elbow 121 must be disconnected from grabber 120.

The above feature is particularly advantageous in that either portion of elongate housing 111 can be replaced or disposed of without requiring replacement or disposal of the other portion. In addition, the foregoing separability makes it possible for either portion to connect to other devices having compatible connections.

In the preferred embodiment of the invention, upper portion 116 is made of metal and lower portion 117 is made of hard, translucent plastic. However, any materials may be used in their construction.

In this embodiment of the invention, implanting member 122 is of the type shown in FIG. 15. That is, as shown in FIG. 16, implanting member 122 preferably includes finger 132, at least a part of which is curved relative to throughbore 124, and which extends beyond blunt end 174. Implanting member 122 includes a slit (see FIG. 17) in between finger 132 and blunt end 174, as does finger 100 shown in FIG. 15, to increase the elasticity of finger 132 during hair implantation, as described above.

In this embodiment, implanting member 122 also includes elbow 121. Elbow 121 may be located at an end of implanting member 122 which is opposite to finger 132, as shown in FIG. 16, or it may be located at any other site along implanting member 122. As shown in FIG. 16A, elbow 121 extends outwardly at roughly a 90° angle from implanting member 122 relative to throughbore 124, so as to permit connection to grabber 120.

To this end, grabber 120 includes jaws 139 and 140, mouth 141, and hole 142. Jaws 139 and 140 open to receive elbow 121 of implanting member 122. That is, upon application of a predetermined amount of pressure to notch 144 between jaws 139 and 140, jaw 139 moves in the direction of arrow 146 and jaw 140 moves in the direction of arrow 147, thereby opening a path to mouth 141. Through this path, elbow 121 of implanting member 122 (see FIG. 16B) is inserted into mouth 141. Once elbow 121 is inserted into mouth 141, jaws 139 and 140 close, thereby holding elbow 121 in place. Hole 142, which is also included on grabber 120, reduces the amount of pressure required to open jaws 139 and 140.

In this regard, elbow 121 is grabbed by grabber 120 in the following manner. That is, assuming that elbow 121 of implanting member 122 is not held by grabber 120, upon actuation of plunger 114, grabber 120 advances forwardly towards elbow 121. The advancement puts pressure on elbow 121, thereby forcing implanting member 122 downwardly within throughbore 124. However, at some point, elbow 121 contacts outer surface 150 of circular magazine 129 (see, e.g., FIG. 17E), thereby stopping the downward motion of implanting member 122. At this point, additional pressure applied to elbow 121 by grabber 120 causes jaws 139 and 140 to open at notch 121. Still further pressure forces elbow 121 within mouth 141.

By holding implanting member 121 using grabber 120, movement of implanting member 122 within throughbore 124 can be controlled by actuation of plunger 114. That is, since plunger 114 controls the movement of grabber 120, and implanting member 122 is held by grabber 120, plunger 114 effectively controls the movement of implanting member 122 within throughbore 124.

To achieve the foregoing, preferably elbow 121 extends beyond width 151 of circular magazine 129, and jaws 139 and 140 of grabber 120 also extend beyond that width. Such a configuration is shown in FIG. 16A. It should be noted, however, that jaws 139 and 140 and elbow 121 need not extend beyond width 151 of circular magazine 129 to accomplish the foregoing.

Since grabber 120 holds onto elbow 121 in the manner described above, at least a portion of throughbore 124 is preferably exposed, as shown, for example, in FIG. 16B and as noted above. This facilitates movement of elbow 121, and thus implanting member 122, within throughbore 124.

As shown in FIG. 16, throughbore 124 includes loading position 154, from which implanting member picks up a loaded hair graft. Loading position 154 is adjacent to throughbore 124, such that implanting member 122 contacts a hair graft therein, as shown in the figures.

As noted above, in this embodiment of the invention, hair grafts are loaded into the loading position by placing a circular cartridge having hair grafts loaded therein into circular magazine 129. In this regard, circular cartridge 156 is inserted into circular magazine 129 face-down, such that hair grafts loaded therein are sandwiched between circular cartridge 156 and circular magazine 129. Thus, circular cartridge 156 includes a flat base, against which hair grafts are placed, and teeth, which separate different hair grafts to be loaded into slots 157, as shown in FIG. 16B. In operation, each of these slots sequentially lines up with loading position 154 to load hair grafts into instrument 110.

By virtue of the foregoing configuration, implanting member 122 can pick up a hair graft loaded by circular cartridge 156 and implant that hair graft into a patient's scalp, as described in more detail below.

As shown in FIG. 16A, circular magazine 129 includes camber 160 at an end of loading position 154, which acts to guide finger 132 into narrow throughbore 161. In this regard, throughbore 124, which extends at least partway up from cutting device 126, includes narrow segment 161 and wide segment 162. Wide segment 162 is located above loading position 154 and narrow segment 161 is located below loading position 154, as shown in FIG. 16A. Thus, prior to loading, implanting member 122, including finger 132, is within wide segment 162. Within wide segment 162, finger 132 which, as noted, is fabricated from a springy material, may or may not be spring-loaded. In any event, upon moving from wide segment 162 into narrow segment 161, finger 132 of implanting member 122 becomes more spring-loaded relative to how it was within wide segment 162. Camber 160, as was the case with camber 60 described above with respect to the second embodiment of the invention, facilitates movement of finger 132 from wide segment 162 into narrow segment 161. That is, camber 160, which preferably has a structure similar to that of camber 60 in the second embodiment, e.g., curved and/or downwardly sloping, guides finger 132 into narrow segment 161 of throughbore 124.

As noted above, circular magazine 129 receives circular cartridge 156 loaded with hair grafts. Circular cartridge 156 preferably advances automatically to a next loaded hair graft each time a hair graft has been implanted and implanting member 122 retracts to above loading position 154. Mechanisms to accomplish such advancement are well-known in the art and, therefore, will not be described in detail herein.

Cutting device 126 is attached to end 164 of lower portion 117 of elongate housing 11, as shown in FIG. 16. Throughbore 124 extends at least part way from cutting device 126, as shown in FIG. 16. Since finger 132 is movable within throughbore 124, finger 132 is movable relative to cutting device 126, as described in more detail below. Preferably, cutting device 126 is a flat blade cutting device, such as that shown in FIGS. 5A and 5B. Other types of cutting devices may be used in this embodiment, however.

Preferred dimensions for some of the foregoing elements are as follows: instrument 110, roughly 8 inches (≈21 centimeters); implanting member 122 including finger 132, roughly 1.75 inches (≈4.5 centimeters); cutting device 126 and finger 132, roughly 0.25 inches (≈0.8 centimeters). These dimensions merely represent dimensions for one possible embodiment and are not meant to limit the invention in any way whatsoever.

FIG. 17, which depicts close-up, side views of a cross-section taken along lines A—A of FIG. 16B, shows movement of implanting member 122 from a first position in which the finger is positioned adjacent to the loading position, to a second position in which a loaded hair graft is bounded between the finger and the cutting device, and then to a third position in which the finger extends beyond the cutting device.

Figure 17A:
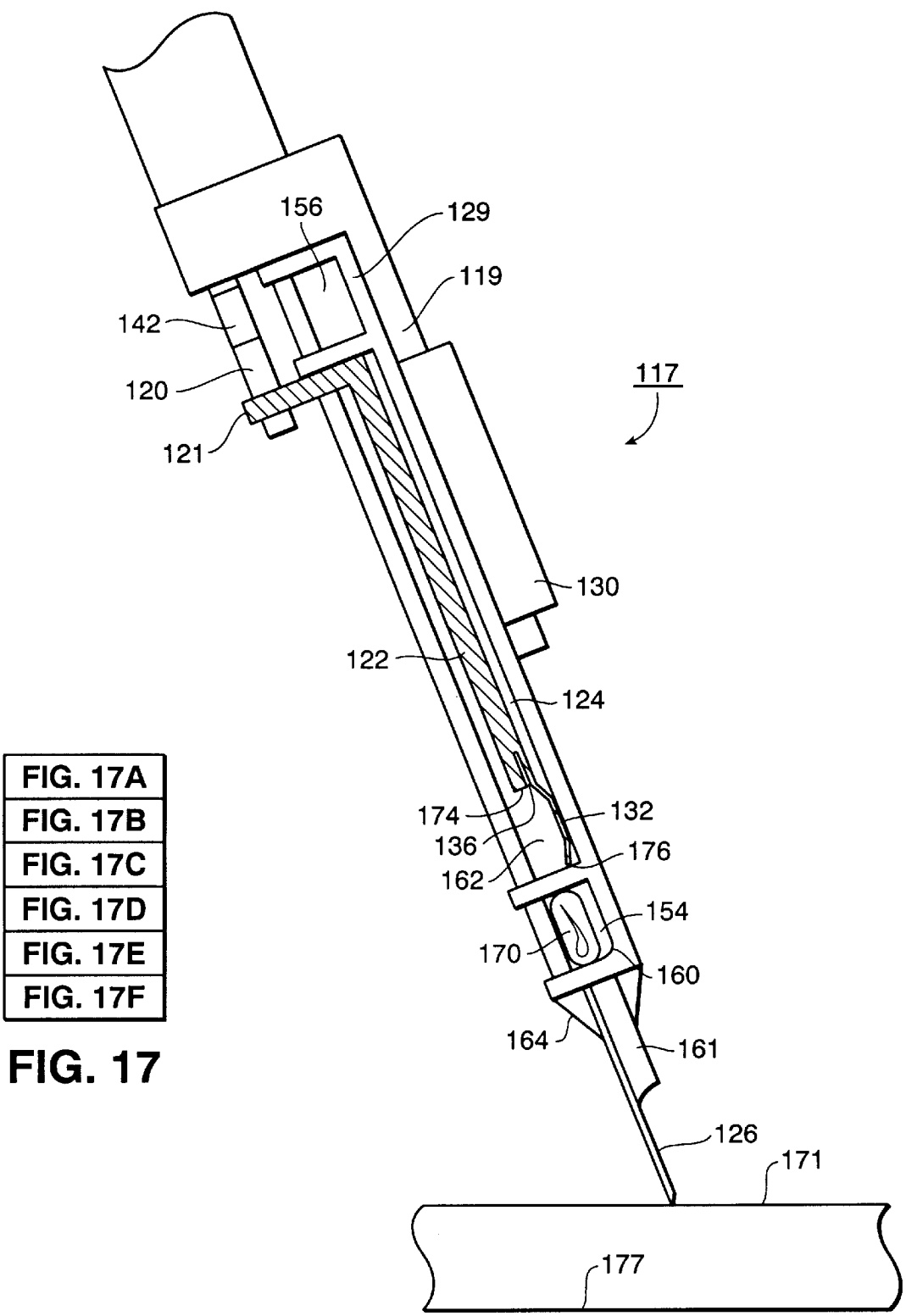
FIG. 17, comprised of FIGS. 17A, 17B, 17C, 17D, 17E and 17F, shows close-up, cross-sectional side views of the fourth embodiment of the hair implanting instrument of the present invention during various stages of a hair transplantation procedure.
Figure 17B:
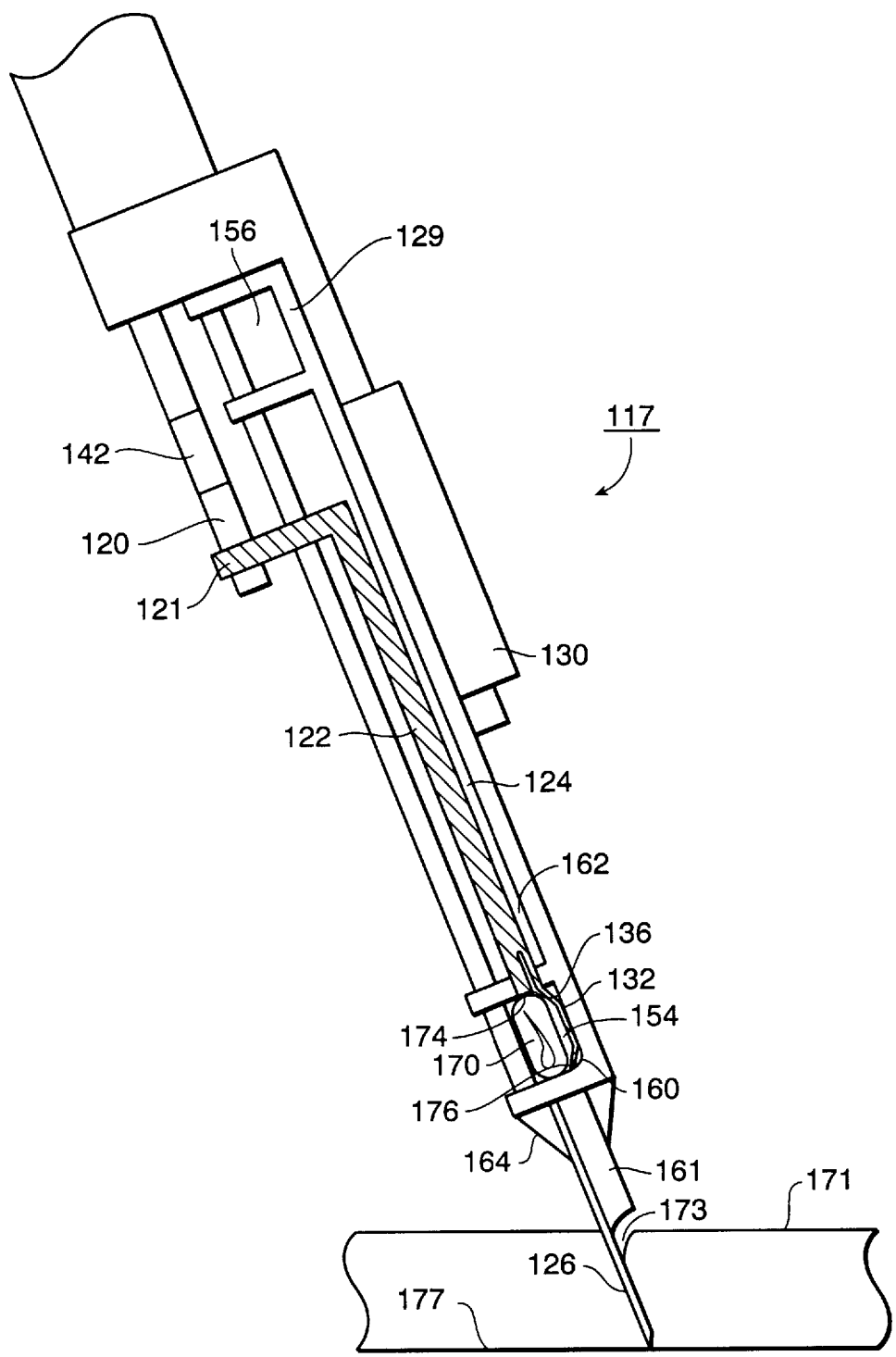

More specifically, FIG. 17B shows a side view of implanting member 122 adjacent to loading position 154. As noted above, implanting member 122 is preferably controlled via grabber 120 by actuating plunger 114 (see FIG. 16). By controlling implanting member 122 thusly, finger 132 can be moved adjacent to hair graft 170 at loading position 154, as was the case above in the first three embodiments of the invention. It is noted that in this case, like in the second embodiment described above, wide segment 162 facilitates movement of finger 132 adjacent to hair graft 170 in loading position 154.

Figure 17C:
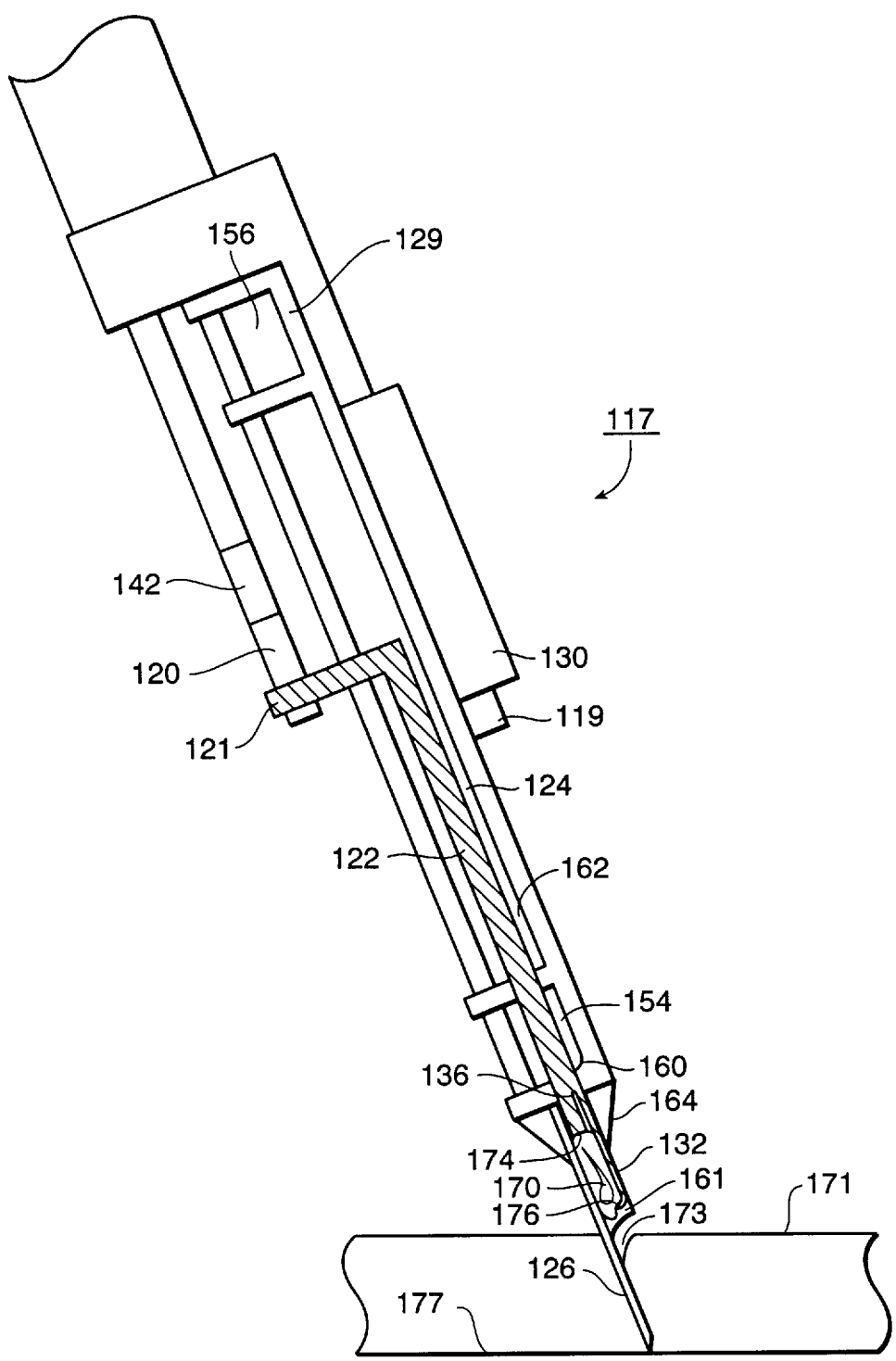
Figure 17D:
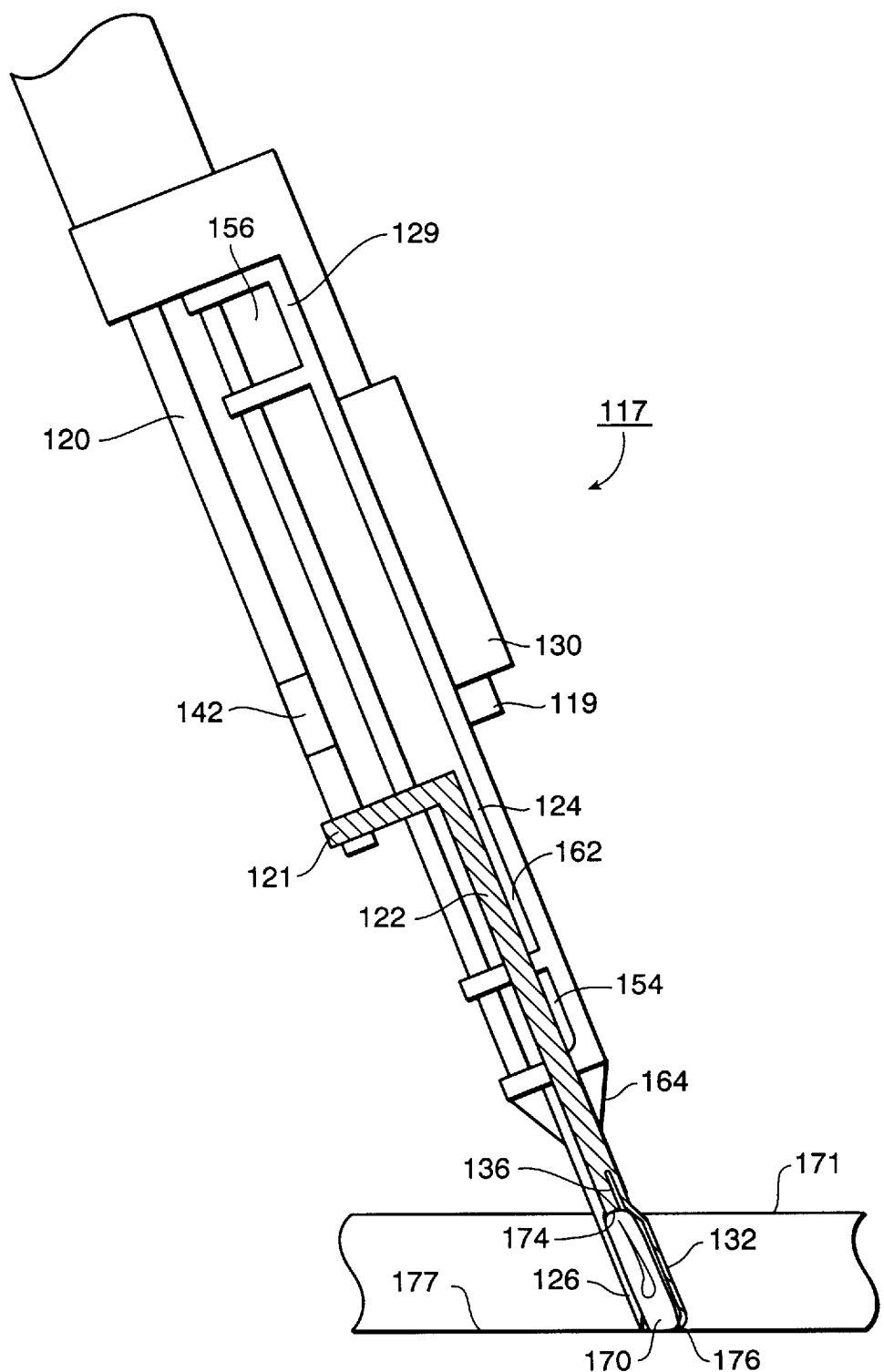

Next, FIG. 17D shows a side view of finger 132 adjacent to cutting device 126, such that hair graft 170 is bounded between finger 132 and cutting device 126. This is the position at which the hair graft, the cutting device, and the finger are in the incision, as described in more detail below.

Figure 17E:
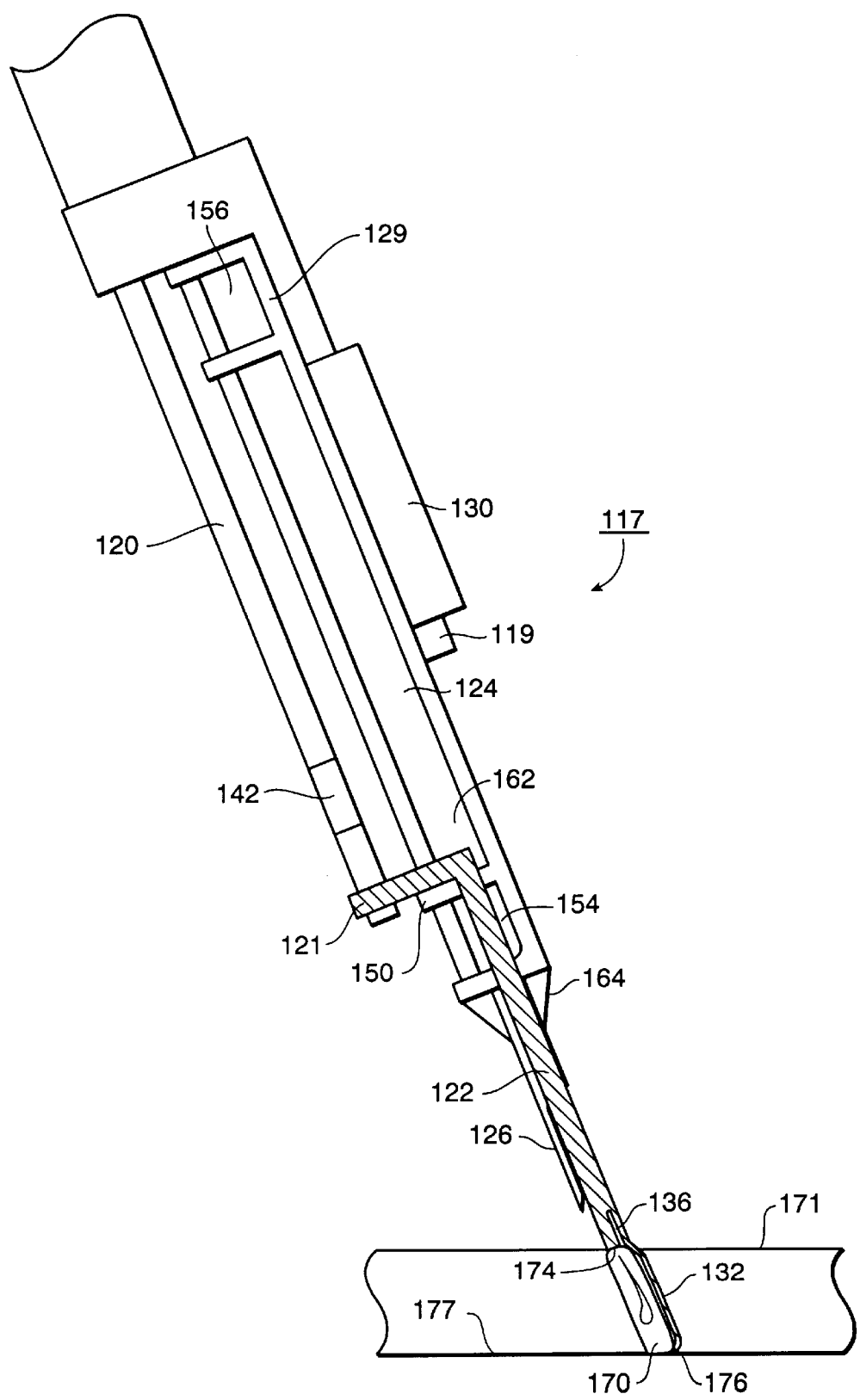
Figure 17F:
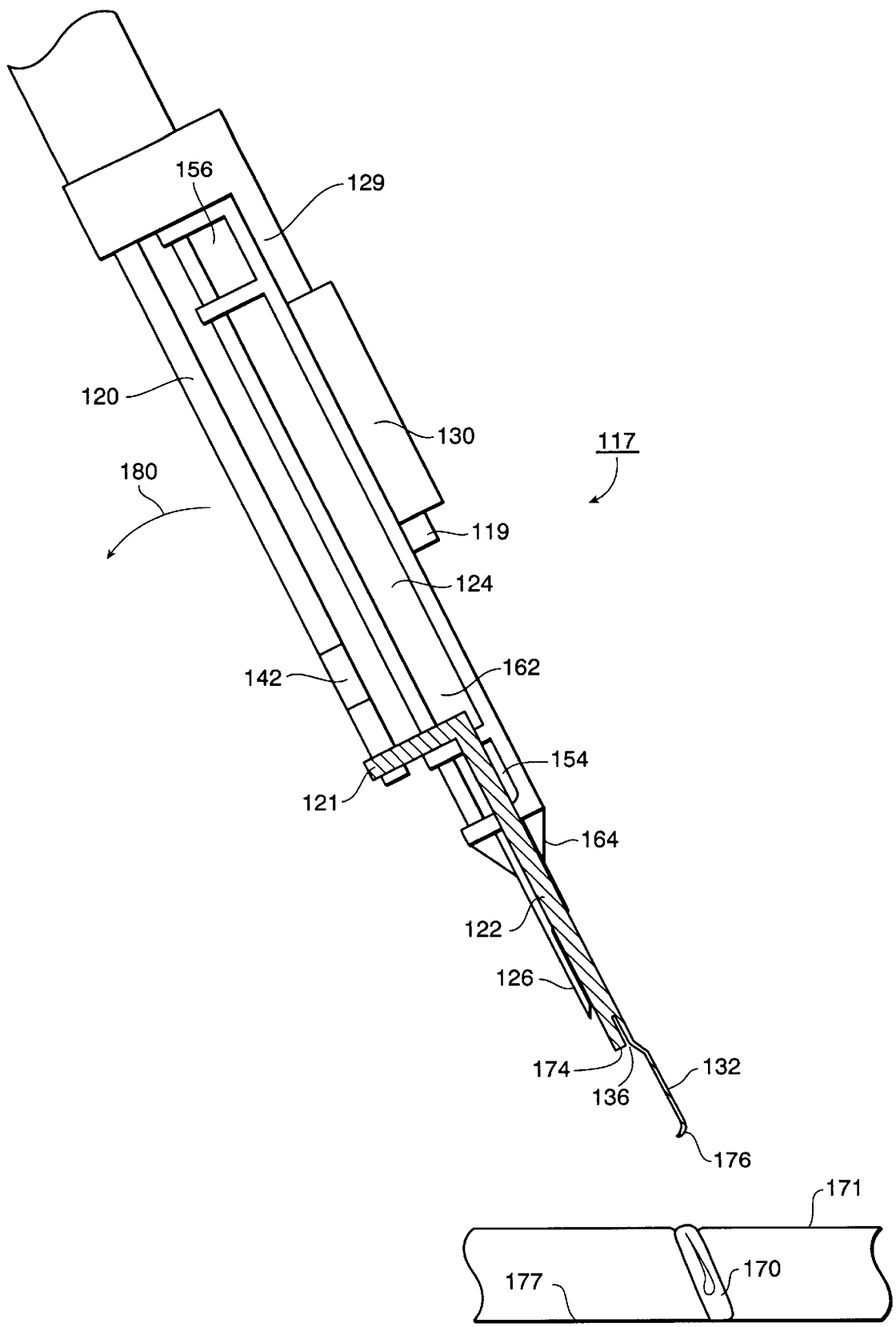

Finally, FIGS. 17E and 17F show side views of finger 132 extending beyond cutting device 126. A description of a hair transplantation procedure using the fourth embodiment of the invention now follows with respect to FIG. 17.

In this regard, FIG. 11 sets forth the steps for a hair transplantation procedure using instrument 110. FIG. 17 graphically depicts the hair transplantation procedure set forth in FIG. 11 using the fourth embodiment of the invention. In this regard, the following description presumes that grabber 120 has already "grabbed hold of" elbow 121 so that movement of implanting member 122 can be controlled by plunger 114. In addition, the following description assumes that a circular cartridge, having at least one hair graft loaded therein, has been inserted into circular magazine 129 such that the hair graft is in loading position 154 and accessible to implanting member 122.

Thus, in step S1101, shown graphically in FIG. 17A, hair graft 170 is placed into loading position 154. As described above, this is done by inserting circular cartridge 156 into circular magazine 129 so that hair grafts loaded into circular cartridge 156 are sandwiched between circular cartridge 156 and circular magazine 129. Thereafter, in step S1102, shown graphically in FIG. 17B, cutting device 126, which in this case is a flat blade-type cutting device, makes incision 173 into patient's scalp 171 in a manner identical to that described in the first to third embodiments of the invention.

In step S1103, also shown graphically in FIG. 17B, and which may or may not be performed at the same time as step S1102, hair graft 170 is loaded into implanting member 122 by advancing implanting member 50 so that finger 132 is adjacent to hair graft 170 in loading position 154. In this embodiment, like in the second embodiment described above, finger 132 is fabricated from a springy material such that it is at least partially expanded within wide segment 162 at loading position 154 (see FIG. 17B). This facilitates loading of the hair graft in step S1103 in the same manner as described above with respect to the second embodiment of the invention.

In this embodiment of the invention, implanting member 122 is identical to that shown in FIG. 15. Thus, finger 132 is separated from blunt end 174 by slit 136. This configuration facilitates compression of finger 132 within narrow segment 161, and expansion of the finger within wide segment 162, as explained above.

In step S1103, camber 160 guides finger 132 from wide segment 162 into narrow segment 161. This causes curved tip 176 of finger 132 to pinch hair graft 170, as shown in FIG. 17C. This pinching action facilitates movement of hair graft 170 from throughbore 124 into the incision in the manner described above with respect to the second embodiment of the invention, e.g., dragging via finger 132 and/or pushing via blunt end 174. Accordingly, a detailed description thereof is omitted for the sake of brevity.

Following step S1103, flow proceeds to step S1104. In step S1104, which is shown graphically in FIG. 17D, implanting member 122 moves hair graft 170 and finger 132 into the incision in scalp 171 such that finger 132 contacts skull 177, and such that hair graft 170 is bounded in the incision by finger 132 and cutting device 126. In doing this, as noted above, finger 132 opens the incision so that the hair graft can more easily be implanted therein.

Flow then proceeds to steps S1105 and S1106, which are similar to their corresponding steps described above for the first to third embodiments. For completeness, FIGS. 17E and 17F are provided, which graphically depict steps S1105 and S1106, respectively. That is, FIG. 17E shows step S1105, in which cutting device 126 is withdrawn from the incision, and FIG. 17F shows step S1106, in which finger 132 is withdrawn from the incision.

In this regard, as was the case above with respect to the second embodiment, in step S1106, finger 132 is preferably withdrawn in a slightly curved direction, roughly along the lines of arrow 180 in FIG. 17F. Finger 132 is withdrawn in this manner so as to reduce the chances that curved tip 176 will not significantly pull hair graft 170 out of the incision during withdrawal of finger 132.

Following step S1106, the process is repeated to implant additional hair grafts in other areas of the patient's scalp.

The present invention has been described with respect to particular illustrative embodiments. It is to be understood that the invention is not limited to the above-described embodiments and modifications thereto, and that various changes and modifications may be made by those of ordinary skill in the art of hair transplanting without departing from the spirit and scope of the appended claims.

What is claimed is:

1. An instrument for implanting hair grafts into a patient's scalp, comprising:

an elongate housing adapted to be manipulated by a surgeon during implanting of the hair grafts, the elongate housing having a throughbore extending at least partway therealong from a first end thereof, and having a slot defining a slotted loading position adjacent to the throughbore for loading hair grafts into the instrument;

a cutting device affixed to the first end of the elongate housing by which the surgeon may make an incision in the patient's scalp, into which a hair graft is to be implanted; and an implanting member, disposed axially movably within the throughbore of the elongate housing, the implanting member including a forwardly projecting finger;

wherein the implanting member is movable from a first position in which the finger is positioned adjacent to the slotted loading position so as to be able to load a hair graft, to a second position in which a loaded hair graft is bounded between the finger and the cutting device, and to a third position in which the finger extends beyond the cutting device.

2. An instrument according to claim 1, wherein the implanting member includes a blunt end which the finger projects beyond.

3. An instrument according to claim 2, wherein the blunt end has a cross-sectional area which is greater than a cross-sectional area of the finger.

4. An instrument according to claim 1, wherein the throughbore comprises at least one narrow segment and a wide segment, the wide segment being adjacent to the loading position; and wherein the finger is fabricated from a springy material, is spring-loaded in at least the narrow segment(s), and is expandable within the wide segment.

5. An instrument according to claim 4, wherein the wide segment and the narrow segment of the throughbore are connected by a camber which includes an inclined surface, and which is capable of guiding the finger from the wide segment of the throughbore into a narrow segment of the throughbore.

6. An instrument according to claim 5, wherein the camber gradually slopes downwardly from the wide segment to the narrow segment.

7. An instrument according to claim 4, wherein the finger includes a tip which is curved relative to an axis of the throughbore.

8. An instrument according to claim 7, wherein the finger is dimensioned to be shorter than the hair graft to be loaded such that the tip of the finger is capable of pinching a loaded hair graft against an inner wall of a narrow segment of the throughbore.

9. An instrument according to claim 7, wherein the finger is dimensioned to be longer than the hair graft to be loaded such that the tip of the finger is capable of shielding at least part of a follicle-end of a loaded hair graft.

10. An instrument according to claim 1, wherein the cutting device comprises a flat blade.

11. An instrument according to claim 1, wherein the cutting device comprises a needle; and wherein a shape of the needle is one of the following: rounded, half-rounded and pointed.

12. An instrument according to claim 1, wherein at least part of the finger is made of polycarbonate steel.

13. An instrument according to claim 1, further comprising an automatic loading mechanism which is capable of loading hair grafts into the slot of the slotted loading position.

14. An instrument according to claim 13, wherein the automatic loading mechanism comprises a linear magazine cartridge which is adapted to store plural hair grafts in plural slots, and which loads the plural hair grafts sequentially from the linear magazine cartridge into the slot of the slotted loading position.

15. An instrument according to claim 13, wherein the automatic loading mechanism comprises a circular magazine cartridge which is adapted to store plural hair grafts in plural slots, and which loads the plural hair grafts sequentially from the circular magazine cartridge into the slot of the slotted loading position.

16. An instrument according to claim 1, wherein the implanting member includes a throughbore at least partway therethrough, and a holding member disposed within the throughbore which is movable relative to the finger; and wherein the holding member is movable from an unextended position, in which the holding member extends to less than a length of the finger, to an extended position, in which the holding member extends to greater than a length of the finger.

17. An instrument according to claim 16, wherein the holding member includes a foot affixed to an end thereof.

18. An instrument according to claim 17, wherein the foot is made of a sponge-like material which is compressible and expandable.

19. An instrument according to claim 1, further comprising a plunger for axially moving the implanting member within the throughbore.

20. An instrument according to claim 1, wherein the elongate housing comprises:

an upper portion which houses a plunger used to control movement of the implanting member, the upper portion including a grabber which holds an end of the implanting member; and a lower portion, which includes the throughbore and houses the implanting member.

21. An instrument according to claim 20, wherein the implanting member comprises an elbow which extends therefrom, and the grabber comprises at least two jaws and a mouth, the two jaws being expandable to allow access by the elbow to the mouth.

22. An instrument according to claim 20, wherein the upper portion and the lower portion of the elongate housing are detachable from each other.

23. An instrument according to claim 20, wherein the lower portion includes a circular magazine adapted to receive a circular cartridge which holds hair grafts to be implanted.

24. An instrument according to claim 1, wherein the implanting member includes a blunt end, the blunt end being separated from the finger by a slit therebetween.

25. An instrument according to claim 24, wherein at least a portion of the finger is curved relative to an axis of the throughbore, and the throughbore includes a wide segment adjacent to the loading position and a narrow segment which extends at least part way up from the cutting device.

26. An instrument according to claim 25, wherein the finger is fabricated from a springy material; and wherein the instrument includes a camber which connects the wide segment to the narrow segment to guide the finger from the wide segment to the narrow segment such that the finger is spring-loaded at least within the narrow segment.

27. A method of implanting a hair graft from a hair implanting instrument into a patient's scalp, comprising the steps of:

making an incision in the patient's scalp using a cutting device, into which a hair graft is to be implanted;

loading a hair graft into an implanting member in the hair implanting instrument, the implanting member being movable relative to the cutting device;

moving the hair graft and a finger projecting forwardly from the implanting member into the incision, such that the hair graft in the incision is bounded by the cutting device and the finger;

a first withdrawing step of withdrawing the cutting device from the incision; and a second withdrawing step of withdrawing the finger from the incision.

28. A method according to claim 27, wherein the implanting member includes a blunt end which the finger projects beyond; and
wherein the loading step comprises the steps of:
inserting the hair graft into a loading position in the hair implanting instrument; and
sliding the implanting member, via a throughbore in the hair implanting instrument, into contact with the hair graft in the loading position so that the finger is adjacent to the hair graft and the blunt end abuts an end of the hair graft.

29. A method according to claim 28, wherein the moving step comprises pushing the hair graft into the incision using the blunt end of the implanting member.

30. A method according to claim 29, wherein the moving step further comprises shielding the hair graft with the finger while the blunt end pushes the hair graft into the incision.

31. A method according to claim 28, wherein the moving step comprises the steps of:
pinching the hair graft between a curved tip of the finger and an inner wall of the throughbore; and
dragging the hair graft into the incision using the finger.

32. A method according to claim 28, wherein the moving step comprises the steps of:
pinching the hair graft between a tip of the finger and an inner wall of the throughbore; and
dragging the hair graft into the incision using the finger while at the same time pushing the hair graft into the incision using the blunt end.

33. A method according to claim 27, wherein the moving step comprises moving the finger into the incision so that the finger contacts the patient's skull.

34. A method according to claim 33, wherein the first withdrawing step comprises the steps of:
applying downward force to the finger against the patient's skull; and
lifting the cutting device out of the incision in response to the downward force applied to the finger, leaving the hair graft and the finger in the incision.

35. A method according to claim 27, wherein the hair implanting instrument member further comprises a holding member movable relative to the implanting member;
wherein the second withdrawing step comprises withdrawing only the finger from the incision; and
wherein the method further comprises the steps of:
sliding the holding member into contact with the hair graft in the incision between the moving and first withdrawing steps; and
withdrawing the holding member from the hair graft after the second withdrawing step.

36. A method according to claim 27, further comprising, between the loading and making steps, the step of automatically loading the hair graft into a loading position, from which the hair graft is loaded in the loading step.

37. A method according to claim 36, wherein the automatically loading step comprises loading hair grafts sequentially from an automatic loading mechanism having either a circular magazine cartridge for storing hair grafts to be loaded or a linear magazine cartridge for storing hair grafts to be loaded.

38. A method according to claim 27, wherein, in the moving step, the finger opens the incision as the finger moves into the incision along with the hair graft.

39. An instrument for implanting hair grafts into a patient's scalp, comprising:

an elongate housing adapted to be manipulated by a surgeon during implanting of the hair grafts, the elongate housing having a throughbore extending at least partway therealong from an incision end thereof, and having an opening defining a loading position for loading hair grafts into the instrument, wherein the opening is disposed adjacent the throughbore and upstream in an implanting direction from the incision end;
a cutting device affixed to the incision end of the elongate housing by which the surgeon may make an incision in the patient's scalp, into which a hair graft is to be implanted; and
an implanting member, disposed axially movably within the throughbore of the elongate housing, the implanting member including a forwardly projecting finger;
wherein the implanting member is movable from a first position in which the finger is positioned adjacent to the opening at the loading position so as to be able to load a hair graft, to a second position in which a loaded hair graft is bounded between the finger and the cutting device, and to a third position in which the finger extends beyond the cutting device.

40. An instrument according to claim 39, wherein the implanting member includes a blunt end which the finger projects beyond.

41. An instrument according to claim 40, wherein the blunt end has a cross-sectional area which is greater than a cross-sectional area of the finger.

42. An instrument according to claim 39, wherein the throughbore comprises at least one narrow segment adjacent the incision end and a wide segment, the wide segment being adjacent to the loading position; and
wherein the finger is fabricated from a springy material, is spring-loaded in at least the narrow segment(s), and is expandable within the wide segment.

43. An instrument according to claim 42, wherein the wide segment and the narrow segment of the throughbore are connected by a camber which includes an inclined surface, and which is capable of guiding the finger from the wide segment of the throughbore into a narrow segment of the throughbore.

44. An instrument according to claim 43, wherein the camber gradually slopes downwardly from the wide segment to the narrow segment.

45. An instrument according to claim 42, wherein the finger includes a tip which is curved relative to an axis of the throughbore.

46. An instrument according to claim 45, wherein the finger is dimensioned to be shorter than the hair graft to be loaded such that the tip of the finger is capable of pinching a loaded hair graft against an inner wall of a narrow segment of the throughbore.

47. An instrument according to claim 45, wherein the finger is dimensioned to be longer than the hair graft to be loaded such that the tip of the finger is capable of shielding at least part of a follicle-end of a loaded hair graft.

48. An instrument according to claim 39, wherein the cutting device comprises a flat blade.

49. An instrument according to claim 39, wherein the cutting device comprises a needle; and
wherein a shape of the needle is one of the following: rounded, half-rounded and pointed.

50. An instrument according to claim 39, wherein at least part of the finger is made of polycarbonate steel.

51. An instrument according to claim 39, wherein the loading position comprises a loading slot.

52. An instrument according to claim 39, further comprising an automatic loading mechanism which is capable of loading hair grafts into the opening of the loading position.

53. An instrument according to claim 52, wherein the automatic loading mechanism comprises a linear magazine cartridge which is adapted to store plural hair grafts in plural slots, and which loads the plural hair grafts sequentially from the linear magazine cartridge into the opening of the loading position.

54. An instrument according to claim 52, wherein the automatic loading mechanism comprises a circular magazine cartridge which is adapted to store plural hair grafts in plural slots, and which loads the plural hair grafts sequentially from the circular magazine cartridge into the opening of the loading position.

55. An instrument according to claim 39, wherein the implanting member includes a throughbore at least partway therethrough, and a holding member disposed within the throughbore which is movable relative to the finger; and wherein the holding member is movable from an unextended position, in which the holding member extends to less than a length of the finger, to an extended position, in which the holding member extends to greater than a length of the finger.

56. An instrument according to claim 55, wherein the holding member includes a foot affixed to an end thereof.

57. An instrument according to claim 56, wherein the foot is made of a sponge-like material which is compressible and expandable.

58. An instrument according to claim 39, further comprising a plunger for axially moving the implanting member within the throughbore.

59. An instrument according to claim 39, wherein the elongate housing comprises:

an upper portion which houses a plunger used to control movement of the implanting member, the upper portion including a grabber which holds an end of the implanting member; and a lower portion, which includes the throughbore and houses the implanting member.

60. An instrument according to claim 59, wherein the implanting member comprises an elbow which extends therefrom, and the grabber comprises at least two jaws and a mouth, the two jaws being expandable to allow access by the elbow to the mouth.

61. An instrument according to claim 59, wherein the upper portion and the lower portion of the elongate housing are detachable from each other.

62. An instrument according to claim 59, wherein the lower portion includes a circular magazine adapted to receive a circular cartridge which holds hair grafts to be implanted.

63. An instrument according to claim 39, wherein the implanting member includes a blunt end, the blunt end being separated from the finger by a slit therebetween.

64. An instrument according to claim 63, wherein at least a portion of the finger is curved relative to an axis of the throughbore, and the throughbore includes a wide segment adjacent to the opening of the loading position and a narrow segment which extends at least part way up from the cutting device.

65. An instrument according to claim 64, wherein the finger is fabricated from a springy material; and wherein the instrument includes a camber which connects the wide segment to the narrow segment to guide the finger from the wide segment to the narrow segment such that the finger is spring-loaded at least within the narrow segment.

* * * * *

UNITED STATES PATENT AND TRADEMARK OFFICE
CERTIFICATE OF CORRECTION

PATENT NO. : 5,817,120

DATED : October 6, 1998

INVENTOR : William R. Rassman

Page 1 of 3

It is certified that error appears in the above-identified patent and that said Letters Patent is hereby corrected as shown below:

COVER PAGE

Under [56], References Cited, U.S. Patent Documents, insert --
```
   1,061,005      5/1913     Parsegan
   1,694,246     12/1928     Boyne
   5,578,054     11/1996     Arnold ........ 606/185--
```

Under [56], References Cited, Other Publications, change "Mar A. Pomerantz," to --Marc A. Pomerantz, et al.--.

Under [56], References Cited, Other Publications, change "The Trauth" to --The Truth--.

COLUMN 5

Line 26, change "that" to --the--.

COLUMN 13

Line 20, change "show" to --shown--.

UNITED STATES PATENT AND TRADEMARK OFFICE
CERTIFICATE OF CORRECTION

PATENT NO. : 5,817,120

DATED : October 6, 1998

INVENTOR : William R. Rassman

It is certified that error appears in the above-identified patent and that said Letters Patent is hereby corrected as shown below:

COLUMN 15

Line 9, change "FIGS. 5a" to --FIGS. 5A--.

COLUMN 16

Line 26, change "FIGS. 5a" to --FIGS. 5A--.

Line 50, change "portion," to --portion 117,--.

Line 59, change "therein A" to --therein. A--.

COLUMN 17

Line 59, change "notch 121." to --notch 144.--

COLUMN 18

Line 65, change "housing 11," to --housing 111--.

UNITED STATES PATENT AND TRADEMARK OFFICE
CERTIFICATE OF CORRECTION

PATENT NO. : 5,817,120

DATED : October 6, 1998

INVENTOR : William R. Rassman

Page 3 of 3

It is certified that error appears in the above-identified patent and that said Letters Patent is hereby corrected as shown below:

COLUMN 19

Line 67, change "member 50" to member 122--.

COLUMN 23

Line 43, delete "member".

Signed and Sealed this

Thirty-first Day of August, 1999

Attest:

Q. TODD DICKINSON

*Attesting Officer*  *Acting Commissioner of Patents and Trademarks*